(12) United States Patent
Eide

(10) Patent No.: US 7,335,162 B2
(45) Date of Patent: Feb. 26, 2008

(54) SYSTEM FOR PERFORMING AN ANALYSIS OF PRESSURE-SIGNALS DERIVABLE FROM PRESSURE MEASUREMENTS ON OR IN A BODY

(75) Inventor: Per Kristian Eide, Oslo (NO)

(73) Assignee: Sensometrics AS, Oslo (NO)

( * ) Notice: Subject to any disclaimer, the term of this patent is extended or adjusted under 35 U.S.C. 154(b) by 0 days.

(21) Appl. No.: 11/600,718

(22) Filed: Nov. 17, 2006

(65) Prior Publication Data

US 2007/0060836 A1 Mar. 15, 2007

Related U.S. Application Data

(60) Division of application No. 10/283,245, filed on Oct. 30, 2002, now Pat. No. 7,198,602, which is a continuation-in-part of application No. 09/843,702, filed on Apr. 30, 2001, now abandoned.

(51) Int. Cl.
*A61B 5/02* (2006.01)
(52) U.S. Cl. .................... 600/485; 600/561
(58) Field of Classification Search ............ 600/485, 600/561
See application file for complete search history.

(56) References Cited

U.S. PATENT DOCUMENTS 4,080,653 A 3/1978 Barnes, Jr. et al.

(Continued)

FOREIGN PATENT DOCUMENTS

WO WO 84/01499 4/1984

OTHER PUBLICATIONS

Eide, et al., Acta Neurochir, vol. 143, pp. 1247 (2001).

(Continued)

*Primary Examiner*—Charles A. Marmor, II
*Assistant Examiner*—Patricia Mallari
(74) *Attorney, Agent, or Firm*—Birch, Stewart, Kolasch & Birch, LLP

(57) ABSTRACT

A system for performing an analysis of pressure-signals derivable from pressure measurements on or in a body of a human being or animal, includes a communication interface for receiving a set of digital pressure sample values, a memory for storing these values, and a processor capable of performing the analysis, the processor having means to identify features related to single pressure waves in the pressure signals based on input of the digital data into the processor, and the processor further having determination means which based on the features is configured to a) determine a minimum pressure value related to diastolic minimum value and a maximum pressure value related to systolic maximum value, b) determine at least one parameter of the single wave parameters elected from the group of: pressure amplitude=$\Delta P$=[(maximum pressure value)−(minimum pressure value)], latency ($\Delta T$), rise time or rise time coefficient=$\Delta P/\Delta T$, and wavelength of the single wave, c) determine number of the single pressure waves occurring during a given time sequence, including determination of the number of single pressure waves with pre-selected values of one or more of the single pressure wave parameters during the given time sequence, and d) determine number of single pressure waves with pre-selected combinations of two or more of the single pressure wave parameters during the given time sequence. Further, the system has a display for visual presentation of the result of analysis performed by the processor.

13 Claims, 12 Drawing Sheets

U.S. PATENT DOCUMENTS

| | | |
|---|---|---|
| 4,186,751 A | 2/1980 | Fleischmann |
| 4,204,547 A | 5/1980 | Allocca |
| 4,295,471 A | 10/1981 | Kaspari |
| 4,338,950 A | 7/1982 | Barlow, Jr. et al. |
| 4,893,630 A | 1/1990 | Bray, Jr. |
| 4,971,061 A | 11/1990 | Kageyama et al. |
| 4,984,567 A | 1/1991 | Kageyama et al. |
| 5,117,835 A | 6/1992 | Mick |
| 5,265,615 A | 11/1993 | Frank et al. |
| 5,533,511 A | 7/1996 | Kaspari et al. |
| 5,873,840 A | 2/1999 | Neff |
| 5,919,144 A | 7/1999 | Bridger et al. |

OTHER PUBLICATIONS

Doyle, D. John et al., Journal of Clinical Monitoring, vol. 8, No. 1, Jan. 1992, pp. 81-90.

Fig. 4

| Stop | Perform analysis | Store | Percentages | Absolute numbers | Calculation 72 of 72 total | | | | | | | |
|---|---|---|---|---|---|---|---|---|---|---|---|---|
| ICP | -10 | -5 | 0 | 5 | 10 | 15 | 20 | 25 | 30 | 35 | 40 | 45 |
| 30 | 0.00 | 0.00 | 846.86 | 845.75 | 796.92 | 325.20 | 107.66 | 37.74 | 18.87 | 12.21 | 9.99 | 8.88 |
| 60 | 0.00 | 0.00 | 536.09 | 536.09 | 505.01 | 198.67 | 69.92 | 31.08 | 13.32 | 11.10 | 9.99 | 7.77 |
| 300 | 0.00 | 0.00 | 177.59 | 177.59 | 159.83 | 72.14 | 26.64 | 6.66 | 4.44 | 2.22 | 1.11 | 0.00 |
| 600 | 0.00 | 0.00 | 68.81 | 68.81 | 65.48 | 18.87 | 8.88 | 3.33 | 2.22 | 1.11 | 0.00 | 0.00 |
| 1200 | 0.00 | 0.00 | 31.08 | 31.08 | 31.08 | 7.77 | 3.33 | 2.22 | 1.11 | 0.00 | 0.00 | 0.00 |
| 2400 | 0.00 | 0.00 | 7.77 | 7.77 | 7.77 | 4.44 | 2.22 | 0.00 | 1.00 | 0.00 | 0.00 | 0.00 |

Time (Seconds)

Recording period (hrs): 9.01     Standardized recording period (hrs): 10.00

Fig. 5

| ICP | -20.00 | -15.00 | 0.00 | 1.00 | 2.00 | 3.00 | 4.00 | 5.00 | 6.00 | 7.00 | 8.00 | 9.00 | 10.00 |
|---|---|---|---|---|---|---|---|---|---|---|---|---|---|
| 10 | 0.00 | 0.00 | 0.00 | 0.00 | 0.00 | 0.00 | 0.00 | 0.00 | 0.00 | 0.00 | 0.00 | 0.00 | 10.00 |
| 15 | 0.00 | 0.00 | 1481.88 | 18.83 | 1.14 | 0.57 | 0.57 | 0.57 | 0.57 | 0.57 | 0.57 | 0.57 | 0.00 |
| 20 | 0.00 | 0.00 | 1235.95 | 10.27 | 0.57 | 0.57 | 0.57 | 0.57 | 0.57 | 0.57 | 0.57 | 0.57 | 0.00 |
| 25 | 0.00 | 0.00 | 1097.29 | 3.42 | 0.57 | 0.57 | 0.57 | 0.57 | 0.57 | 0.57 | 0.57 | 0.00 | 0.00 |
| 30 | 0.00 | 0.00 | 1024.82 | 2.28 | 0.57 | 0.57 | 0.57 | 0.57 | 0.00 | 0.00 | 0.00 | 0.00 | 0.00 |
| 35 | 0.00 | 0.00 | 959.20 | 0.57 | 0.57 | 0.57 | 0.57 | 0.57 | 0.00 | 0.00 | 0.00 | 0.00 | 0.00 |
| 40 | 0.00 | 0.00 | 928.96 | 0.57 | 0.57 | 0.57 | 0.57 | 0.57 | 0.00 | 0.00 | 0.00 | 0.00 | 0.00 |
| 45 | 0.00 | 0.00 | 917.55 | 0.57 | 0.57 | 0.57 | 0.00 | 0.00 | 0.00 | 0.00 | 0.00 | 0.00 | 0.00 |
| 50 | 0.00 | 0.00 | 879.32 | 0.57 | 0.57 | 0.00 | 0.00 | 0.00 | 0.00 | 0.00 | 0.00 | 0.00 | 0.00 |

Time Seconds

Recording period (hrs): 17.52

Standardized recording period (hrs): 10.00

SYSTEM FOR PERFORMING AN ANALYSIS OF PRESSURE-SIGNALS DERIVABLE FROM PRESSURE MEASUREMENTS ON OR IN A BODY

This application is a Divisional of application Ser. No. 10/283,245, filed on Oct. 30, 2002 now U.S. Pat. No. 7,198,602, which is a Continuation-in-Part of U.S. application Ser. No. 09/843,702, filed on Apr. 30, 2001 now abandoned, the entire contents of each of which are hereby incorporated by reference and for which priority is claimed under 35 U.S.C. § 120. This nonprovisional application also claims priority under 35 U.S.C. § 119(a) on International Application PCT/N002/00164 filed on Apr. 29, 2002 under the Patent Cooperation Treaty, the entire contents of which are hereby incorporated by reference.

BACKGROUND OF THE INVENTION

1. Field of the Invention

The present invention relates to a system for performing an analysis of pressure-signals derivable from pressure measurements on or in a body of a human being or animal, as defined in the preamble of attached claim 1. The invention provides for monitoring and analyzing of pressure within body cavities in a human body or animal body, e.g., intracranial pressure and blood pressure, and even in cavities such as e.g. cerebrospinal fluid space. The invention provides for analysis of pressure signals subsequent to sampling, recordal, storage and processing of pressure measurement signals, and thereby quantitative analysis.

BACKGROUND OF THE INVENTION

2. Related Art

The clinical use of intracranial pressure monitoring was first described by Janny in 1950 and Lundberg in 1960.

Intracranial pressures may be measured by different strategies. Solid or fibre-optic transducers may be introduced into the epidural or subdural spaces, or introduced into the brain parenchyma. Intracranial pressure also may be recorded directly by measuring pressure in the cerebrospinal fluid, requiring application of catheter to the cerebrospinal fluid space (most commonly in the cerebral ventricles or the lumbar spinal cavity). During infusion tests the pressure in the cerebrospinal fluid is recorded.

The present invention deals with strategies to analyze single pulse pressure waves, and make analysis of these waves available to the daily clinical practice. The fluctuations of intracranial pressure arise from cardiac and respiratory effects. The intracranial pressure cardiac waves or cerebrospinal fluid pulse waves result from the contractions of the left cardiac ventricle. The intracranial pressure wave or the cerebrospinal fluid pulse wave resemble the arterial blood pressure wave, that is characterized by a systolic rise followed by a diastolic decline and a dicrotic notch. In addition, changes in pressures associated with the respiratory cycle affect the intracranial pressure wave. The morphology of the intracranial pulse pressure wave depends on the arterial inflow, venous outflow, as well as the state of the intracranial contents. The single pulse pressure waves of intracranial pressure include three peaks that are consistently present, corresponding with the arterial pulse waves. For a single pulse pressure wave the maximum peak is termed P1 or top of the percussion wave. During the declining phase of the wave, there are two peaks namely the second peak (P2), often termed the tidal wave, and the third peak (P3), often termed the dicrotic wave. Between the tidal and dicrotic waves is the dicrotic notch that corresponds to arterial dicrotic notch. In the present application, the amplitude of the first peak ($\Delta P1$) is defined as the pressure difference between the diastolic minimum pressure and the systolic maximum pressure, the latency of the first peak ($\Delta T1$) is defined as the time interval when pressures increases from diastolic minimum to systolic maximum. The rise time ($\Delta P1/\Delta T1$)) is defined as the coefficient obtained by dividing the amplitude with the latency. The morphology of the single pulse pressure wave is intimately related to elastance and compliance. Elastance is the change in pressure as a function of a change in volume, and describes the effect of a change in volume on intracranial pressure. Compliance is the inverse of elastance and represents the change in volume as a function of a change in pressure. Therefore, compliance describes the effect of a change in pressure on craniospinal volume. Elastance is most useful clinically as elastance describes the effect of changes in intracranial volume on intracranial pressure. The relationship between intracranial pressure and volume was described in 1966 by Langfitt and showed an exponential curve, where the slope of any part of the curve resembles the rise time of a single wave (that is $\Delta P/\Delta T$ or change in pressure/change in volume). The curve is termed the pressure-volume curve or the elastance curve. The horizontal part of the curve is the period of spatial compensation whereas the vertical portion is the period of spatial decompensation. When elastance increases also the amplitude of a single pulse pressure wave increases due to an increase in the pressure response to a bolus of blood from the heart. It has, however, not been possible to take the knowledge of single wave parameters into daily clinical practice.

In the intensive care unit, continuous intracranial pressure monitoring usually presents the pressures as mean pressure in numerical values, or as a curve that has to be visually analyzed. Though single waves may be displayed on the monitor, strategies to explore trends in changes of single wave characteristics are lacking. Furthermore, strategies to continuously examine compliance solely on the basis of the pressure curves have not been established.

There is a close relationship between blood pressure and intracranial pressure as the intracranial pressure waves are built up from the blood pressure waves. Simultaneous assessment of intracranial pressure and blood pressure provides several advantages, for instance by calculation of the cerebral perfusion pressure (that is mean arterial pressure minus intracranial pressure). The assessment of cerebral perfusion pressure represents a critical parameter in the monitoring of critically ill patients. Assessment of blood pressure per se also has a major place in daily clinical practice, including both assessments of diastolic and systolic pressures.

SUMMARY OF THE INVENTION

The technical solution may be applied to a variety of pressures such as intracranial pressures (or cerebrospinal fluid pressures), blood pressures, or other body cavity pressures. Invasive or non-invasive sensors may record pressures.

According to the invention, the intracranial pressure curve is quantified in different ways. The pressure recordings may be presented as a matrix of numbers of intracranial pressure elevations of different levels (e.g. 20, 25 or 30 mmHg) and durations (e.g. 0.5, 1, 10 or 40 minutes), or a matrix of numbers of intracranial pressure changes of different levels and durations. The pressure recordings also may be presented as a matrix of numbers of single pulse pressure waves of certain characteristics. In this context, elevations are understood as rises in pressure above the zero level that is relative to the atmospheric pressure. An elevation of 20 mmHg represents the pressure of 20 mmHg relative to the atmospheric pressure. Pressure changes represent the differences in pressures at different time stamps. A pressure change of 5 mmHg over a 5 seconds period represents the differences in pressure of 5 mmHg over a 5 seconds measuring period. It should be understood that each pressure recording is measured along with a time stamp. All pressure signals are measured along a recording time. Similar analysis can be made for blood pressure and cerebral perfusion pressure.

With regard to sampling, analysis and presentation of single pulse pressure waves, relative differences in pressures and relative time differences are computed. The analysis is not relative to the zero level or the atmospheric pressure, therefore the results of data analysis are not affected by the zero level or drift of zero level.

By means of the invention used as stated above, the applicant was able to show in a study including 127 patients that the calculation of mean intracranial pressure is an inaccurate measure of intracranial pressure. There was a weak correlation between mean intracranial pressure and the number of intracranial pressure elevations. A high proportion of abnormal intracranial pressure elevations may be present despite a normal mean intracranial pressure. In another study including 16 patients undergoing continuous intracranial pressure monitoring before and after cranial expansion surgery, the applicant found that calculation of numbers of intracranial pressure elevations of different levels and durations in a sensitive way revealed changes in intracranial pressure after surgery. Comparing mean intracranial pressure before and after surgery did not reveal these changes. Accordingly, this type of quantitative analysis of the intracranial pressure curve represents a far more accurate and reliable way of analyzing intracranial pressure than the classical ways of analyzing mean intracranial pressure and describing Lundberg's A, B or C waves.

With regard to single pulse pressure waves, the invention provides measurement and analysis of the following parameters:
a) Minimum is defined as the diastolic minimum pressure of the single wave, or as the valley of the wave.
b) Maximum is defined as the systolic maximum pressure of the single wave, or defined as the peak of the wave.
c) Amplitude is defined as the pressure difference between the systolic maximum pressure and the diastolic minimum pressures during the series of increasing pressures of the single wave.
d) Latency is defined as the time of the single wave when the sequence of pressures increases from minimum pressure to maximum pressure.
e) Rise time is defined as the relationship between amplitude divided by latency, and is synonymous with the rise time coefficient.
f) Wavelength is defined as the duration of the single pulse pressure wave when pressures changes from minimum and back to minimum, and reflects the heart rate.

As mentioned in the Related Art section, amplitude, latency and rise in the present invention is referring to the first peak (P1). This does not represent a limitation of the scope of the invention, however, as amplitude, latency and rise time also may be calculated for the second (P2) and third (P3) peaks as well.

By means of the invention the applicant showed that quantitative analysis of characteristics of single pulse pressure waves revealed important and new information about the pressures. Both these latter parameters are important for assessment of abnormal pressures. The applicant has demonstrated (not published) that parameters of the single pulse pressure waves analyzed and presented quantitatively, provide information about compliance and elastance.

The quantitative method was developed for various pressures such as blood pressure, intracranial pressure (subdural, epidural, intraparenchymatous, or cerebrospinal fluid pressure), and cerebral perfusion pressure.

Furthermore, the quantitative method was developed for offering different types of data presentations:
a) matrix presentations of numbers or percentages of single pulse pressure waves with pre-selected characteristics during a recording period,
b) graphical presentations of single pulse pressure waves with the opportunity to compare single waves, either between individuals, against a reference material or within the same individual at different time intervals,
c) various types of statistical handling of the data are possible.

According to the invention, the system includes:
a communication interface for receiving a set of digital pressure sample values,
a memory for storing these values, and
a processor capable of performing the analysis,
said processor having means to identify features related to single pressure waves in said pressure signals based on input of said digital data into the processor,
said processor further having determination means which based on said features is configured to:
a) determine a minimum pressure value related to diastolic minimum value and a maximum pressure value related to systolic maximum value,
b) determine at least one parameter of the single wave parameters elected from the group of: pressure amplitude=$\Delta P$=[(maximum pressure value)−(minimum pressure value)], latency ($\Delta T$), rise time or rise time coefficient=$\Delta P/\Delta T$, and wavelength of the single wave,
c) determine number of said single pressure waves occurring during a given time sequence, including determination of the number of single pressure waves with pre-selected values of one or more of said single pressure wave parameters during said given time sequence, and
d) determine number of single pressure waves with pre-selected combinations of two or more of said single pressure wave parameters during said given time sequence, and
a display for visual presentation of the result of analysis performed by the processor.

Further embodiments of the system, according to the invention, are defined in sub-claims 2-13.

One object of the present invention is to provide a technical solution for continuous digital sampling of pressures in a body cavity such as intracranial pressure, with or without simultaneous blood pressure measurement, in freely moving individuals that are not bed-ridden. Therefore the apparatus is small and may be driven by a rechargeable battery.

In the context of the invention there is disclosed apparatus to provide for recordal of signals indicative of the intracranial pressure or blood pressure from various sources of signals, that is invasive implanted microtransducers and non-invasive devices using acoustic or ultrasonic signals, or other signals recorded by non-invasive devices. Thus, the algorithm for analysis of pressures may be used whether pressure signals are derived from invasive or non-invasive devices.

The invention is useful for monitoring intracranial pressures without being dependent on the zero level (i.e. calibration against the atmospheric pressure). This is particularly important for pressure sampling by means of non-invasive sensors. An object of the invention is to provide a solution for analysis and presentation of continuous intracranial pressure recordings obtained by non-invasive sensors.

Another object of the present invention is to provide a new method of analyzing pressure samples such as intracranial pressure, blood pressure or cerebral perfusion pressure, including quantitative presentations of the various pressure curves. The different pressures may be monitored simultaneously.

Through use of proper software it is possible to perform software for the quantitative analysis and presentation of continuous pressure recordings representing e.g. intracranial pressure, blood pressure and cerebral perfusion pressure. The software has several options for quantitative description of the data, including calculation of a matrix of pressure elevations of different levels and durations, or a matrix of pressure changes of different levels and durations, or a matrix of numbers of single pulse pressure wave parameters with selected characteristics.

The main objectives of the invention are related to intracranial pressure and blood pressure, but this is not a limitation on the scope of the invention. The invention can also be utilized in connection with pressure sensors measuring pressure in other body cavities (such as the cerebrospinal fluid cavities).

In a process for obtaining pressure signals and carrying out analysis thereof, one or more pressure sensors are applied to a patient and the pressure signals from the sensors are sampled at selected intervals. The sampled signals are converted to digital form and stored along with a time reference that makes it possible to evaluate the change of pressure over time. The time reference may be stored as part of the digital value, or it may be associated with the memory position, or memory address, at which the pressure value is stored. The stored sample values are then, according to this embodiment of the invention, analyzed in order to generate a presentation of at least one of the following: number of pressure elevations with any selected combination of level and duration; number of pressure changes with any selected combination of level difference and duration of change; and number of pulse pressure waves with preselected characteristics regarding minimum, maximum, amplitude, latency and rise time. This allows for various sampling rates and duration of measuring periods. Assessment of single pulse pressure waves preferentially requires a sampling rate of 100 Hz or above. As an alternative to numbers, percentages may be computed. Any point of the single waves may be calculated, and different parameters of the waves may be computed. There is a fundamental difference between computation of number of pressure elevations with any selected combination of level and duration and number of pulse pressure waves with preselected characteristics regarding minimum, maximum, amplitude, latency and rise time. One way is thereby to compute pressures relative to a zero level (i.e. atmospheric pressure), whereas a second way is to compute relative differences in pressures and time and therefore is independent on the zero level.

In the context of the invention there is provided a system for handling single pulse pressure waves in a way that pressures from a single subject may be superimposed on the pressure-volume (elastance) curve providing information about the elastance. This solution provides one of several strategies of early detection of decompensation of pressures, before the conventional methods.

In the present disclosure there is described a system for quantitative and accurate comparisons of pressure recordings/curves when assessing pressure in a body cavity or blood pressure. Comparisons may be made between different continuous pressure curves that include different recording periods, different heart rates, as well as different zero levels. Comparisons of continuous pressure recordings may be made both between individuals and within individuals (that is before and after treatment or comparisons of pressure recordings at different time intervals). This system makes use of a newly developed algorithm (not further disclosed) in computer software. The algorithm includes quantitative approaches for analysis of the pressure recordings and strategies to present the recordings. The system may be integrated in commercially available pressure transducer devices, in computer servers or in medical device computers or in the portable apparatus for pressure monitoring described here.

The technical solution of comparing various continuous pressure curves involves standardisation procedures. The numbers/percentages during a given recording period may be standardized to numbers/percentages during a standardized recording period (e.g. one or 10 hours) and a standardized heart rate. For different individuals the quantitative data for a given recording period may be standardised to a selected recording period (for example numbers/percentages during one minute, one hour or 10 hours recording period), as well as standardised to a selected heart rate (for example heart rate of 60 each minute). Thereby, continuous pressure recordings for different individuals may be compared. This strategy may provide the opportunity for development of reference curves, on the basis of recordings in several individuals. Comparisons of pressure curves for individual cases also become possible. During real time and on-line pressure monitoring, changes in pressure trends may be explored. For example, numbers of pressure characteristics during one hour of pressure recording may be compared at different time intervals.

As compared to the traditional monitoring of mean intracranial pressure, assessment of parameters of single waves may provide early warning of changes in brain compliance, allowing early intervention to reduce pressure.

In the context of the invention, there is disclosed a system for performing the analysis according to the method. The system may be in the form of a suitably programmed computer, or dedicated equipment particularly designed for performing this analysis. The system includes a communication interface for receiving a set of digital pressure sample values, a memory for storing these values, and a processor for performing the analysis described above. The system further includes a video interface that is controlled by the processor and that is capable of generating a visual presentation of the result of any analysis performed by the processor. The visual presentation will be presented on a display. The system also comprises input means for allowing a user to change the parameters of the performed analysis. This implies that the system may be integrated in different computer servers, medical device computers or vital sign monitors. Therefore, the apparatus described here represents no limitation by which the invention may be applied.

The output computed by the software may be presented in a number of ways, including matrix of numbers, graphical presentations, and comparisons of pressures in an individual against a reference material or against previous recordings of the individual.

The particular features of the invention are described in the attached independent claims, while the dependent claims describe advantageous embodiments and alternatives.

Further exemplifying features and embodiments of the invention as well as other aspects of and relations thereto will now be described in the following description with reference to the attached drawings.

BRIEF DESCRIPTION OF THE DRAWINGS

FIG. 4 shows a part of the graphical user interface of FIG. 3 for different levels and duration's.

FIG. 5 is a graphical user interface for presenting pressure-sampling results.

DETAILED DESCRIPTION OF PREFERRED EMBODIMENTS

Figure 1:
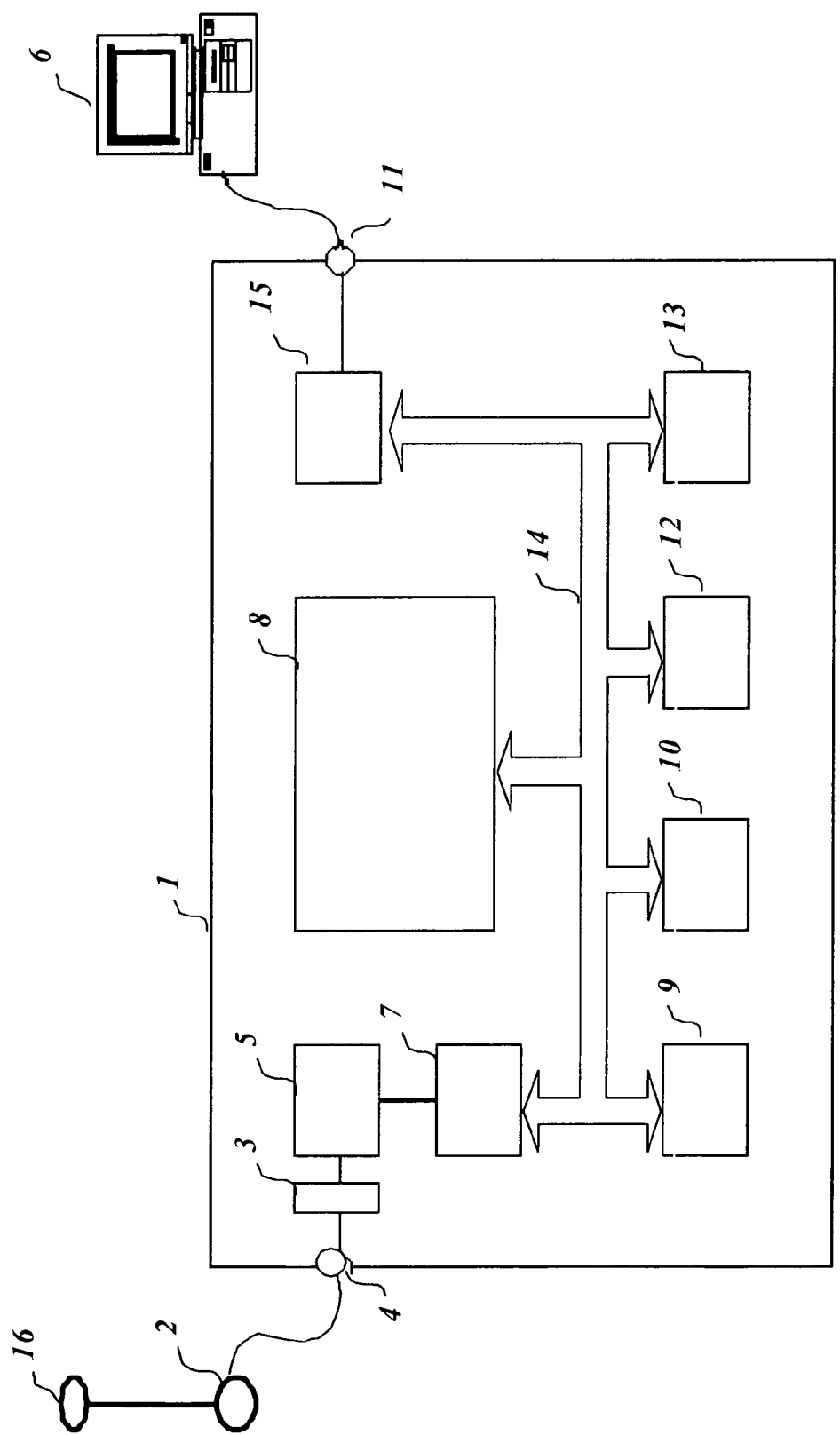
FIG. 1 is a block diagram of the various components of a system according to the invention.

FIG. 1 illustrates in a block diagram a system for measuring pressure in a body cavity of a patient. The main components of this system includes a pressure sensor 16, a pressure transducer 2, a portable apparatus for measuring and storing pressure values 1, and a network station such as a personal computer 6 for receiving and processing registered pressure values. The apparatus 1 is a digital system with a central processing unit 8 for sampling and storing pressure measurements in a patient, such as intracranial pressure, blood pressure or pressure in other body cavities or blood pressure. In the following example an embodiment for measuring intracranial pressure will be described, but it must be understood that this is not a limitation on the scope of the invention.

As a result of its compact construction and lightweight, a patient can easily carry the apparatus 1. The apparatus 1 may be fastened to the belt of the patient or kept in a carry pouch with straps. Alternatively, the apparatus 1 may be used as an interface for connecting the network station or personal computer 6 to the pressure sensor 2. This allows real time online monitoring of pressure so that the pressure curves may be displayed on a display. The different applications of the apparatus 1 as well as modifications in the construction of the apparatus 1 are further illustrated in FIG. 11.

Most commercially available sensors 16 give an analogue signal on the basis of a mechanical action on the sensor. Within the pressure transducer 2 the signals from the sensor is converted to a signal that may either be a voltage or current signal. The pressure transducer 2 then produces a continuous voltage or current signal. The voltage or current signals from the transducer are further processed within the signal conditioner 5. The analogue signals are converted to digital signals within the analogue to digital converter 7. Certainly various modifications are possible. When data are collected from for example a vital signs monitor both the pressure transducer 2 and the analogue to digital converter 7 may be built into the vital signs monitor. The digital signals are handled according to the invention.

The apparatus 1 may be constructed in a number of ways. The embodiment described below is based on a unit with a central processing unit 8 operating in accordance with instructions stored in memory 9 and communicating with the various parts of the apparatus over a common data bus 14. However, a number of variations are possible. Instead of using a central processing unit 8 and instructions stored in memory 9, the functionality of the apparatus 1 could be constructed directly in hardware, e.g. as ASICs. The apparatus represents no limitation for the use of the system for the analysis and presentation of pressures described here.

The main components of the apparatus 1 are then the analog to digital converter 7, which converts the received analog measuring signals to digital, the data memory 9, which receives the digitized values from the analog to digital converter 7 and stores them. An input/output interface 15 allows data stored in the memory 9 to be transferred to the network station or personal computer 6 for processing. The apparatus preferably includes a galvanic element 3 protecting the patient from the electric circuitry of the apparatus, a signal conditioner 5 either to the input or the output of the analog to digital converter 7, an input control 10 for controlling operation and adjusting settings of the apparatus, a display unit 12, and an alarm unit 13. Input control 10, display 12 and alarm unit 13 are connected to and in communication with the central processing unit 8 and/or other parts of the apparatus such as ASICs, display drivers, and power sensors (not shown).

Besides, the software computes the number of artifacts during a recording period, and the artifact ratio. The program includes an option for excluding recordings when the artifact ratio is above a selected level.

After the signal conditioner 5 has processed the analog signals, the analog signals are converted to digital signals within an analog to digital converter 7. The central processing unit 8 controls the operation of the various elements of the apparatus 1. The central processor is in communication with the analog to digital converter 7, and is capable of reading out samples of the digitally converted pressure measurements and storing them in a data memory 9. The data memory 9 may be in the form of electronic circuits such as RAM, or some form of magnetic storage, such as a disc, or any other convenient form of data memory known in the art.

As has already been mentioned, the apparatus 1 is here described as receiving signals indicative of the intracranial pressure from sensors 16 implanted within the skull. However, the apparatus may also incorporate a signal conditioner 5 for processing signals from non-invasive devices such as acoustic, ultrasonic or Doppler devices. Whether the entire apparatus 1 must be constructed with a signal conditioner 5 for a specific purpose or whether the same signal conditioner 5 allows for different uses, with or without re-programming, is dependent on implementation and specific needs. If the apparatus 1 is intended to work with various sensors 16 with various levels of sensitivity, the signal conditioner should be adjustable in a manner that allows operation with the desired sensors and to adapt the output range to the various sensors to the input range of the analog to digital converter 7. In this case the signal conditioner 5 must obviously be connected between the input of the apparatus 1 and the analog to digital converter 7.

The apparatus 1 is programmable including an input control 10, with a simple key board for entering a few commands. The input control 10 has a calibration function that allows calibration of the pressure sensor 16 against the atmospheric pressure, before the sensor 2 is implanted within the skull of the patient. Thereby the intracranial pressure monitored actually is the difference between the atmospheric pressure and the pressure within the skull of the patient. It should be noted, however, that this invention also describes a method for recording and analysis of relative continuous pressure recordings that are not related to the atmospheric pressure, and are independent of a zero level. The input control 10 also contains a function for selecting the interval of pressure recordings. The pressures may be recorded with variable sampling frequency, e.g. from about 1-10 Hz up to at least 150 Hz (most preferably between 100 and 200 Hz). When single pulse pressure waves are monitored, the sampling frequency preferentially is 100 Hz or above. The minimum memory space should then allow storing of recordings at least 150 times a second for at least 48 hrs (26 920 000 recordings). The input control 10 preferably also has a function for adjusting the real time clock, since each pressure sample should include a time reference indicating when the sample was made.

Via a connector 11, data may be transferred to the personal computer 6 for analysis. The connector 11 may be a serial port, and the apparatus will preferably comprise an input/output interface 15 converting the internal signal format for the apparatus 1 to a format for communication over said connector 11.

A display 12 shows on-line the digital pressure signals as well as the real-time time. The display 12 is preferably controlled by the central processing unit 8.

An internal battery (not shown) powers the apparatus 1 that preferably is rechargeable, but with input for external power supply (not shown).

In a preferred embodiment, the apparatus 1 has an alarm function that indicates shortage of memory capacity or reduced battery capacity. This alarm may be displayed visually on the display 12, but may also include a unit 13 emitting an audible alarm signal.

Figure 11:
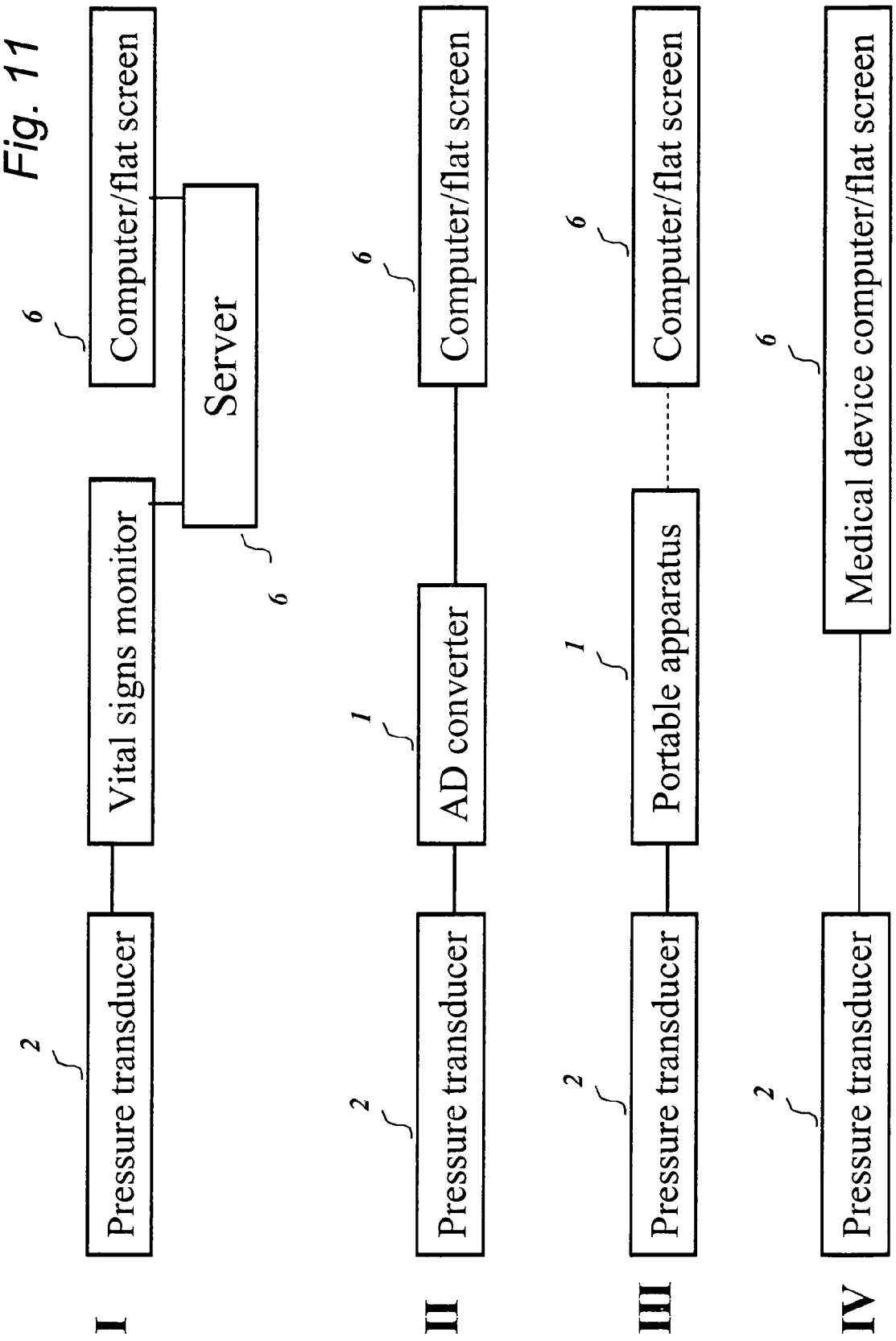
FIG. 11 presents for three different patients the pressure curves and the accompanying histograms of single wave distribution.

As mentioned before, the apparatus 1 may be connected to a personal computer 6 via the serial port 11. Alternatively the apparatus 1 may be connected to another digital computer-based monitoring system 6 such as a network station. This gives the opportunity for on-line and real time monitoring of the pressure with real time graphic presentation of the recordings. In this situation the apparatus 1 functions as an interface for a stationary personal computer or flat screen. Different applications are illustrated in FIG. 11.

The apparatus 1 is preferably controlled by software that is stored in a non-volatile part of the memory 9, and that controls the operation of the central processor 8. The various units of the apparatus are shown as communicating over a common data bus 14, but it should be noted that the various components may be interconnected in other ways.

The invention also relates to a method for measuring and analyzing pressure in a patient. This method will now be described.

First a signal from a pressure sensor 16 and transducer 2 representative of pressure in a body cavity is received and sampled at selected intervals. This signal is converted to digital form 7 and stored along with a time reference representative of the time at which the sample was made 9. The time reference does not have to be a time reference value stored for every sample. Since the sample rate will be known, it will be sufficient to store an actual time reference for the start of the measuring period. The time reference for the individual samples will then be given by their relative address in memory.

The stored sample values may then be analyzed in order to generate a presentation regarding a time period of at least one of the following:
  number of pressure elevations with any selected combination of level and duration,
  number of pressure changes with any selected combination of level difference and duration of change,
  number of single pulse pressure waves with pre-selected characteristics such as minimum, maximum, amplitude, latency and rise time.

This type of analysis may be performed either on-line or off-line. During on-line analysis, analysis is performed repeatedly and presented repeatedly during real-time on-line monitoring. This allows for comparisons of pressure characteristics at repeated intervals. Off-line analysis is performed after the recording period has been ended.

In order to analyze number of pressure elevations with any selected combination of level and duration occurring in a time period, the stored samples are simply analyzed in order to determine for how long the measured pressure has remained within a certain pressure interval. According to a preferred embodiment of the invention, the user performing the analysis will be able to set the pressure intervals defining the various levels and duration of pressure elevations manually and perform the analysis repeatedly with different values for these parameters. Level may be measured on a linear scale e.g. with intervals of 5 mmHg, while the time scale intervals should preferably increase with time, e.g. each interval being twice as long as the previous shorter interval.

An analysis of number of pressure changes with any selected combination of level difference and duration of change would involve an analysis of the stored samples in order to determine the size of a pressure change and the time over which the change takes place.

An analysis of single pulse pressure waves will take into consideration not only elevations that remain within a certain time interval, but the transition of a wave from minimum to maximum and back to a new minimum or vice versa. Pre-selected characteristics identifying a pressure wave of interest may be the duration of the single pulse wave from minimum (maximum) back to minimum (maximum) combined either with minimum value, maximum value or amplitude of the single wave. Another pre-selected characteristic may be the rise time of the single wave.

The pressure sensor 16 may be applied by implanting the sensor in a body cavity of the patient, but it may also be applied by a non-invasive technique with a sensor using acoustic measuring signals, ultrasonic or Doppler, or even a pressure sensor for measuring blood pressure. In general, a problem with non-invasive sensors recording intracranial pressure, is the lack of a zero level since intracranial pressure is calibrated against atmospheric pressure. The present invention solves this problem by computing the relative differences in pressure during single pressure wave analysis. Thereby the need for a zero level is excluded.

According to a preferred embodiment, the sampling rate is at least 10 Hz, and the measurements may be taken over a period of at least 24 hours. Even more preferably, the measurements may be performed with a sampling rate of 100 Hz, or at least 150 Hz, and taken over a period of at least 48 hours. According to the preferred embodiment of the apparatus the physician can set the sampling rate through the input control 10.

The computer is not shown in detail. It preferably includes a standard communication interface for receiving a set of digital pressure sample values from the apparatus described above, as well as data memory, such as a hard drive, for storing the received sample values and processing means, such as a microprocessor, with access to said data memory, and capable of analyzing said sample values in order to determine at least one of the following:

number of pressure elevations with any selected combination of level and duration—number of pressure changes with any selected combination of level difference and duration of change,—number of single pulse pressure waves with preselected characteristics regarding minimum, maximum, amplitude, latency and rise time. The computer further includes a video interface in communication with said processing means and capable of, in combination with the processor means, generating a visual presentation of the result of any analysis performed on the pressure sample values together with a graphical user interface. The video interface may be a graphics card connected to a display for displaying the generated visual presentation. The computer will also include input means allowing a user of the system to enter and change parameters on which said analysis should be based. These input means will normally include a keyboard and e.g. a mouse, and the user will be assisted by a graphical user interface presented on the display.

The parameters on which the analysis should be based may include at least some of the following: pressure intervals defining a number of pressure elevations, pressure change intervals defining a number of pressure change step sizes, time intervals defining a number of durations, pressure wave characteristics including minimum, maximum, amplitude and latency, selection of type of analysis, and selection of presentation of numbers as absolute numbers, percentages or numbers per time unit.

The operation of the computer 6 will preferably be controlled by computer program instructions stored in the computer 6 and making the computer capable of performing the analysis. The program will preferably be able to perform the analysis based on default values in the absence of parameters input by a user. Such a computer program may be stored on a computer readable medium such as a magnetic disc, a CD ROM or some other storage means, or it may be available as a carrier signal transmitted over a computer network such as the Internet.

Figure 2:
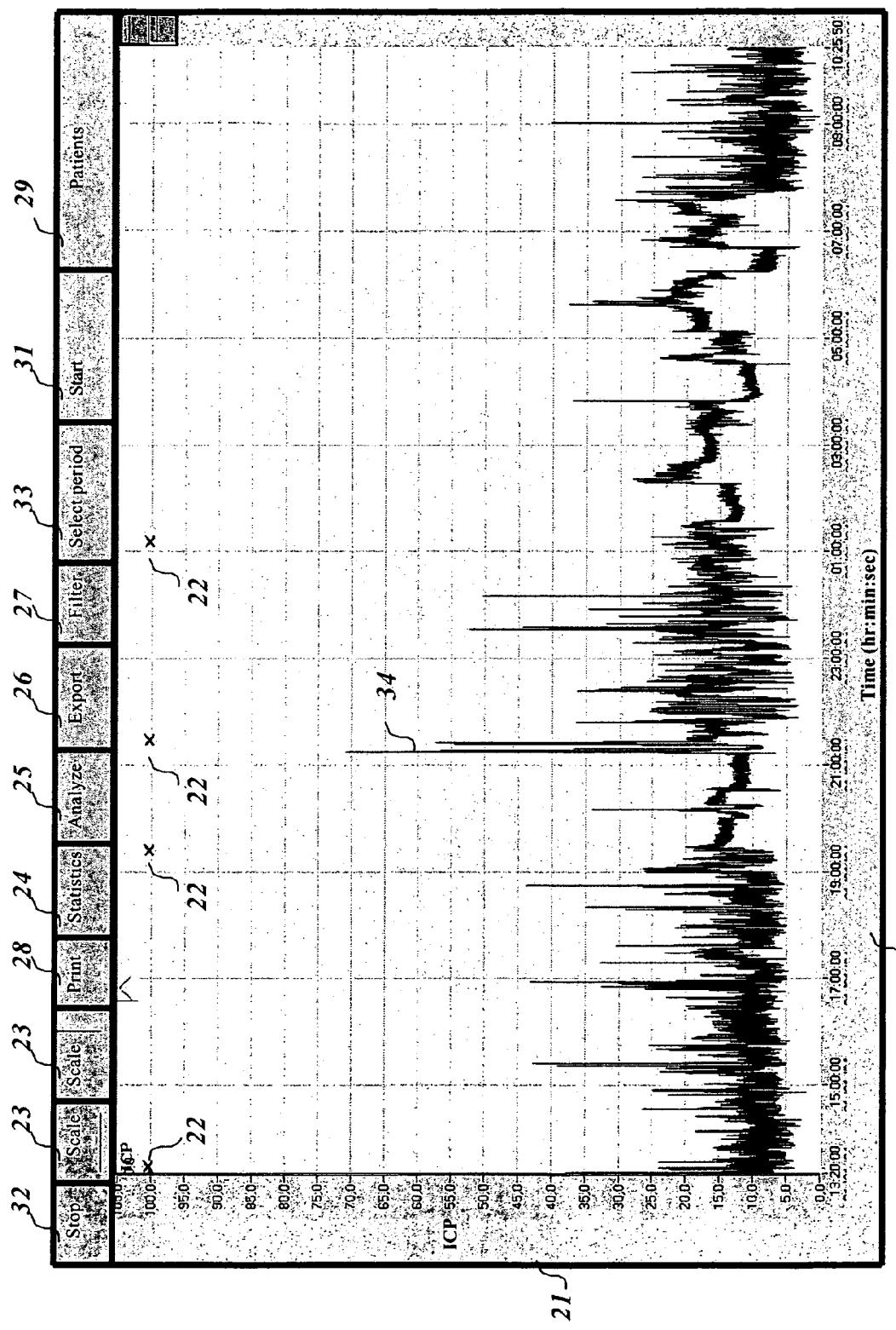
FIG. 2 is a graphical user interface used for presenting pressure-sampling results.

FIG. 2 illustrates the graphical user interface of the computer software used for presenting the results of the sampling described above. The software processes the digital pressure signals. Before the continuous pressure recordings are presented in the graphical user interface as shown in FIG. 2, the pressure signals are sampled and averaged. With regard to FIG. 2, the sample update rate was in the range 30 to 100 Hz and the update rate (average interval) was in the range 1 to 5 seconds. The update rates may vary between 1-10 Hz for low frequency sampling. Modern vital signs monitors may offer a computer interface producing this type of averaging. Various modules of the software generate output or can be invoked through this interface. The intracranial pressure curve 34 may be presented in various windows. The X-axis shows the time of registration 20, that is real time of intracranial pressure sampling (presented as hours: minutes: seconds). The Y-axis 21 shows the absolute intracranial pressure recordings (presented as mmHg). During the recordings, it is possible to mark events (e.g. sleep, walking, sitting) and these may be presented as symbols 22 along the X-axis above the pressure graph. There are functions 33 for selecting the recording periods, for instance selecting parts of the intracranial pressure curve during sleep, walking, sitting etc. There are functions for selecting different window sizes 23 both vertically and horizontally. The curve 34 presented in the window in FIG. 2 represents about 21 hours recording time (that is actual recording time). A special function 24 allows simple statistical analysis of the data presented in the window (with calculations of mean, standard deviation, median, ranges and time of recording). Another function 25 transfers to a software module that performs quantitative analysis of a single intracranial pressure curve in accordance with the invention. The results of this analysis are described below with reference to FIGS. 3-6. Another function 26 allows export of intracranial pressure data from a selected window to files with a selected text format such as ASCII, that can be utilized by e.g. spreadsheet or word processing applications. The intracranial pressure curve may be smoothened by another function 27. Another function allows printing of the intracranial pressure curve 28. The software also includes a function for patient identification 29 also containing some data of the patient (such as tentative diagnosis and cause of examination). In addition, there are start 31 and stop 32 buttons for controlling the sampling process. If the apparatus has collected pressure samples from several pressure transducers 2, e.g. intracranial and blood pressure, these may be simultaneously analyzed. The functions are linked up to the pressure recordings displayed in the window. Any type of pressure may be presented in this way.

The size of the window, that is the observation time may be changed to reveal the single pulse waves. Each single pulse wave is built up from a blood pressure wave. Comparable to the heart rate, during one minute of recording often about 50-70 single pulse waves may be recorded. There is, however, a large variation in heart rate both between and within individuals, accordingly there is a variation in the numbers of single pulse intracranial or blood pressure waves during one minute recording.

The graphical interface in FIG. 2 represents one example of presenting/displaying the various functions. Various modifications are possible. Simultaneous presentations of the continuous pressure recording curves of different pressures (e.g. intracranial pressure, blood pressure, cerebral perfusion pressure) may be presented in the same window. The continuous recordings are presented real time so that the different types of pressures may be compared. Modifications in the graphical interface may be performed whether the pressure monitoring is intended for on-line or off-line monitoring. During on-line monitoring, statistical analysis may be computed repeatedly, to allow comparisons between different time intervals. The real-time continuous pressure curve may be presented in one window, the absolute pressure parameters (such as mean pressure, standard deviation, and ranges) in another window and single waves in still another window.

The functions referred to above and the software modules that perform them will not be described in detail as they are well known in the art and do not constitute a part of the invention as such.

Figure 3:
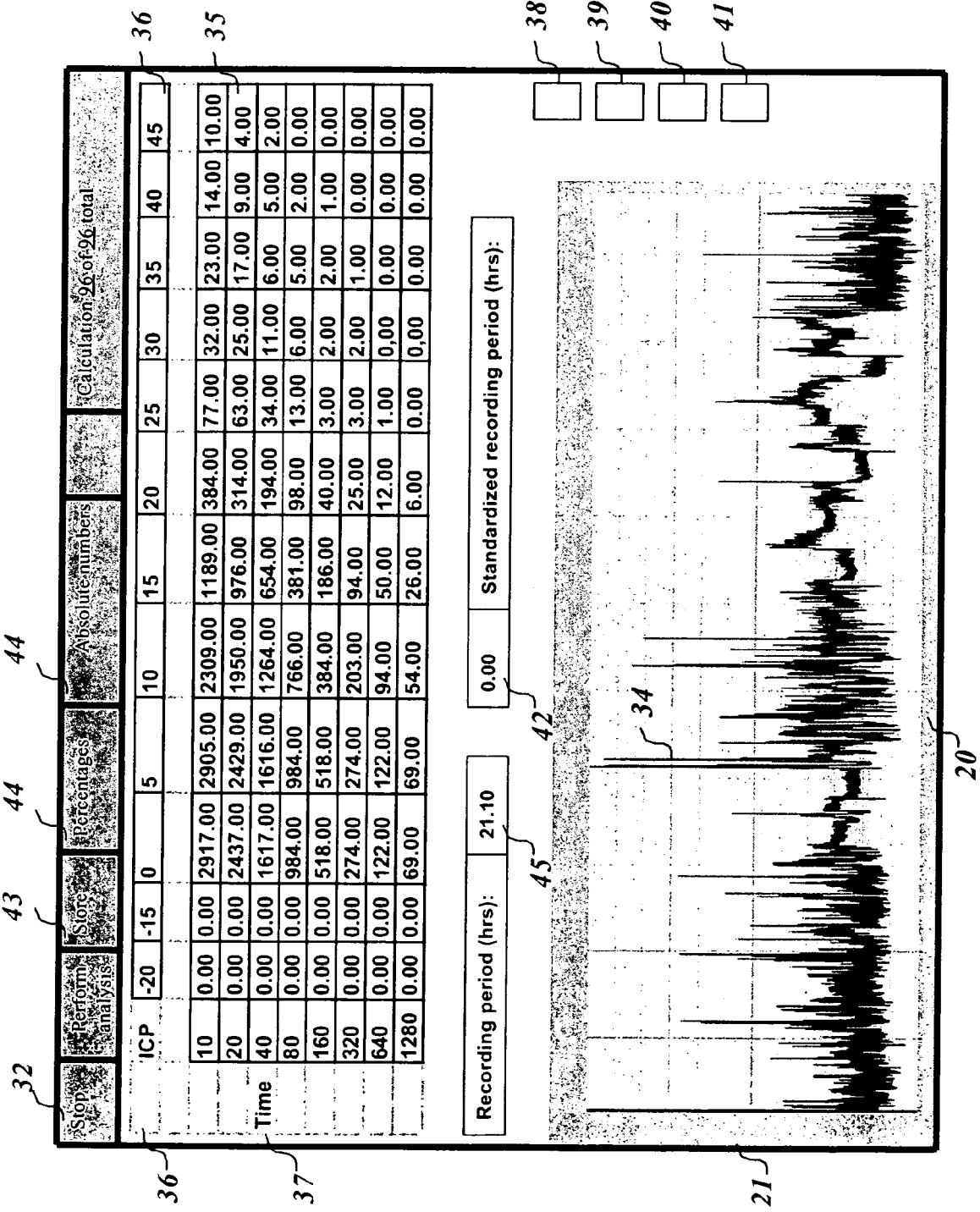
FIG. 3 is a graphical user interface for presenting and controlling the analysis of a pressure curve.

Reference is now made to FIG. 3 which shows the graphical user interface of the software module for analysis of the intracranial or blood pressure curve, or other pressures in human body cavities. The selected window of the intracranial pressure curve 34 is presented as a chart or matrix 35 of quantities of different types, derived through the invented method of analysis. Any size of the recording period 33 represented by the window may be selected for the quantitative analysis. A similar user interface is used independent on the type of pressure measured.

The mathematical functions may be implemented in the software by various routes. One implementation is shortly described. The data needed for analysis of pressure elevations of different levels and durations include the pressure recordings and the corresponding time recordings. Two variables are selected, namely the threshold levels (pressures expressed in mmHg) and the width (time expressed in seconds). A search is made for both peaks (positive-going bumps) and valleys (negative-going bumps), and the exact levels of peaks and valleys are identified. Peaks with heights lower than the threshold or valleys with troughs higher than the thresholds are ignored. For a threshold value less or equal to zero a valley search is performed. For threshold values greater than zero a search for peaks is performed. The peak/valleys analysis is performed for every width/threshold combination in the matrix. In short, the procedure is as follows. The part of the pressure curve 34 that is to be examined is selected 33, the data is visualised in the user interface. A suitable width/threshold matrix is selected, specifying the width/threshold combinations. The units used are time in seconds (width) 37, and pressure in mmHg (threshold) 36, respectively. The software records the numbers of samples that fit a given width/threshold combination. The output from the analysis is a matrix containing the numbers of all the different width and threshold combinations. An example of such a matrix 35 is given in FIG. 3. As shown in the matrix 35, the width/threshold combination 20 seconds/25 mmHg (that is ICP elevations of 25 mmHg lasting 20 seconds) occurred 63.00 times during the actual recording time of 21.10 hours 45. In this matrix the numbers were not standardised to a selected recording period 42. The pressure elevations are relative to the zero level that corresponds to the atmospheric pressure.

By clicking a first button 38, the user can select a presentation of the data as a chart of numbers of intracranial pressure elevations with various combinations of level 36 and duration 37. The intracranial pressure levels and durations may be selected in each case. According to a preferred embodiment, intracranial pressure is expressed as mmHg and duration as seconds and minutes. Also blood pressure may be expressed as mmHg. Independent of the type of pressure measured the pressures may be presented in the same way.

A second button 39 allows the user to select presentation of the data as a chart of numbers of intracranial pressure intracranial pressure changes of different levels 36 and duration 37. The changes may be differences between two recordings or differences between a recording compared to a given or selected value (e.g. mean pressure).

By clicking a third button 40, the user selects presentation of the data as numbers of single pulse pressure waves with pre-selected characteristics. The user accesses an input dialog box for entering these characteristics by clicking a fourth button 41. Each single pulse pressure wave is identified by minimum, maximum, amplitude, latency and rise time. Further details about analysis and presentation of the parameters of single pulse pressure waves are given in FIGS. 7-10.

The presentation of the results of the analysis in chart 35 may be toggled between absolute numerical quantities and percentages of recording time by clicking one of two buttons 44.

The numbers may be standardized by presenting the data as numbers per time unit 42. The time unit (e.g.) may be selected in each individual case. The data presented in FIG. 3 was based on a recording time of 21.1 hrs (actual recording time 45), and the recordings were not standardized in this case (represented by zero in standardization input box 42). It should be noted that standardization may be performed to various time units, such as each one minute, one hour or even 10 hours. Since the calculation of single pulse pressure waves automatically also gives the heart rate it is possible to standardize the numbers according to a given heart rate (further details given in FIG. 7). For example, the numbers may be standardized to a given heart rate of 60/min.

During on-line presentation the matrix 35 may be compared repeatedly. The whole matrix 35 may not need to be presented but only certain width/threshold combinations. Differences between certain combinations at different time intervals may be revealed. For example, the numbers or percentages of intracranial pressures of 15, 20 and 25 mmHg lasting 5 minutes during 1 hour recording period may be computed and presented each hour during on-line presentation. Normalization of data to a standardized recording time 42 and heart rate allows for accurate comparisons between different time intervals for individual cases, as well as comparisons between individuals.

For example, for blood pressure, comparisons of pressure curves may be performed before and after treatment with medications in an individual. Alternatively, pressure recordings from an individual may be compared against a normal material. A normal material may be constructed on the basis of the recordings from a large group of individuals.

The method for performing these analyses is described above, and the various buttons described above invokes software modules for performing the various steps of this method.

Again, a special function 43 allows the analyzed data to be saved as text files with a selected text format such as ASCII, or other files compatible with applications for mathematical and/or statistical handling of the data or for generating presentations.

FIG. 4 shows part of the graphical user interface of FIG. 3 with a different set of parameters. In particular, the various time intervals of duration 37 have been changed, and the matrix 35 shows numbers of elevations normalized as number of occurrences per time unit 42. In this case the numbers are derived from a standardized recording time of 10 hours 42, with the actual recording period 9.01 hrs 45.

The results shown in FIG. 3 are the results of an analysis of number of pressure elevations with selected combinations of level and duration. As indicated in FIG. 4, the stored samples have been analyzed in order to determine for how long the measured pressure level 36 has remained within a certain pressure interval, represented as −10, −5 0, 5, 10, 15, 20, 25, 30, 35, 40 and 45 mmHg relative to atmospheric pressure, for certain periods of time 37. The various periods of time 37 are selected as 30, 60, 300, 600, 1200 and 2400 seconds, respectively. In FIG. 4, the results have been normalized to numbers during a 10 hours recording period 42. Among the results in the result matrix 35 it can be seen that intracranial pressure elevations of 45 mmHg with a duration of 30 seconds have occurred 8.88 times when normalized to a 10 hour measuring period. Similarly, pressure elevations of 30 mmHg with a duration of 600 seconds have occurred 2.22 times when normalized to a 10 hrs recording period. In FIG. 3, where the results are not normalized, all the results are integers.

During the standardisation procedure, the numbers or percentages are adjusted to a given factor. The normalised time may be chosen in each individual. An example is given. If the actual recording time is 6 hours, a standardisation to 10 hours recording time implies that all numbers or percentages of pressure elevations are multiplied with a factor equal to $10/6$ (that is 1.66666).

The following example is intended to illustrate various aspects of the present invention regarding related measurements of pressure waves described in FIGS. 2-4, but is not intended to limit the scope thereof.

EXAMPLE 1

Continuous intracranial pressure monitoring was performed in a girl aged 2 years and 11 months because of suspected shunt failure. In this girl an extracranial shunt was previously placed because of hydrocephalus. Shunt failure was suspected because of headache, lethargy and irritability. In fact, increased, reduced or normal intracranial pressures may cause these symptoms. The results of intracranial pressure monitoring during sleep in this girl were as follows: Mean intracranial pressure 14.4 mmHg, range 0.1-67.3 mmHg, std 5.7 mmHg. The duration of intracranial pressure monitoring was 544 minutes. A mean pressure of 14.4 mmHg is by most physicians considered as borderline whereas a pressure above 15 mmHg is considered as abnormal. Therefore, no indication for surgery (shunt revision) was found on the basis of the intracranial pressure monitoring. The girl was not treated which resulted in lasting symptoms of headache and lethargy for more than 2 years. A retrospective analysis of the intracranial pressure curve was performed by means of the method according to the invention. FIG. 4 shows a matrix of intracranial pressure elevations of different levels and durations that was calculated, clearly demonstrating a high number of abnormal intracranial pressure elevations, for instance a high number of intracranial elevations of 25 mmHg or above. During a standardized recording time of 10 hours, intracranial pressure elevations of 25 mmHg lasting 300 seconds occurred 6.66 times. Such elevations generally are considered as abnormal. This case serves as an example of an intracranial pressure curve that was misinterpreted because the curve was interpreted on the basis of classical criteria. Mean intracranial pressure was within acceptable values. Application of the present software added significant new information that would have changed the decision making in this patient.

FIG. 5 shows the same part of the graphical user interface as FIG. 4, but in this case the analysis is an analysis of number of pressure with selected combinations of level difference 30 and duration of change 37. The stored samples have been analyzed in order to determine the number of pressure changes of certain sizes 30, represented as −20, −15, 0, 1, 2, 3, 4, 5, 6, 7, 8, 9 and 10 mmHg relatively, and the duration 37 over which these changes take place, given as 10, 15, 20, 25, 30, 35, 40, 45 and 50 seconds. Among the results given in the result matrix 35 it can be seen that a pressure change of 2 mmHg that takes place over a 15 seconds has occurred on average 1.14 times per 10 hour period. Changes of 0 mmHg represent periods of time over which the pressure has remained constant. Also in this matrix the numbers have been standardized to numbers during a 10 hours recording period. The standardization procedure gives the opportunity to compare pressure curves, either within individuals at different time intervals or between individuals.

Figure 6:
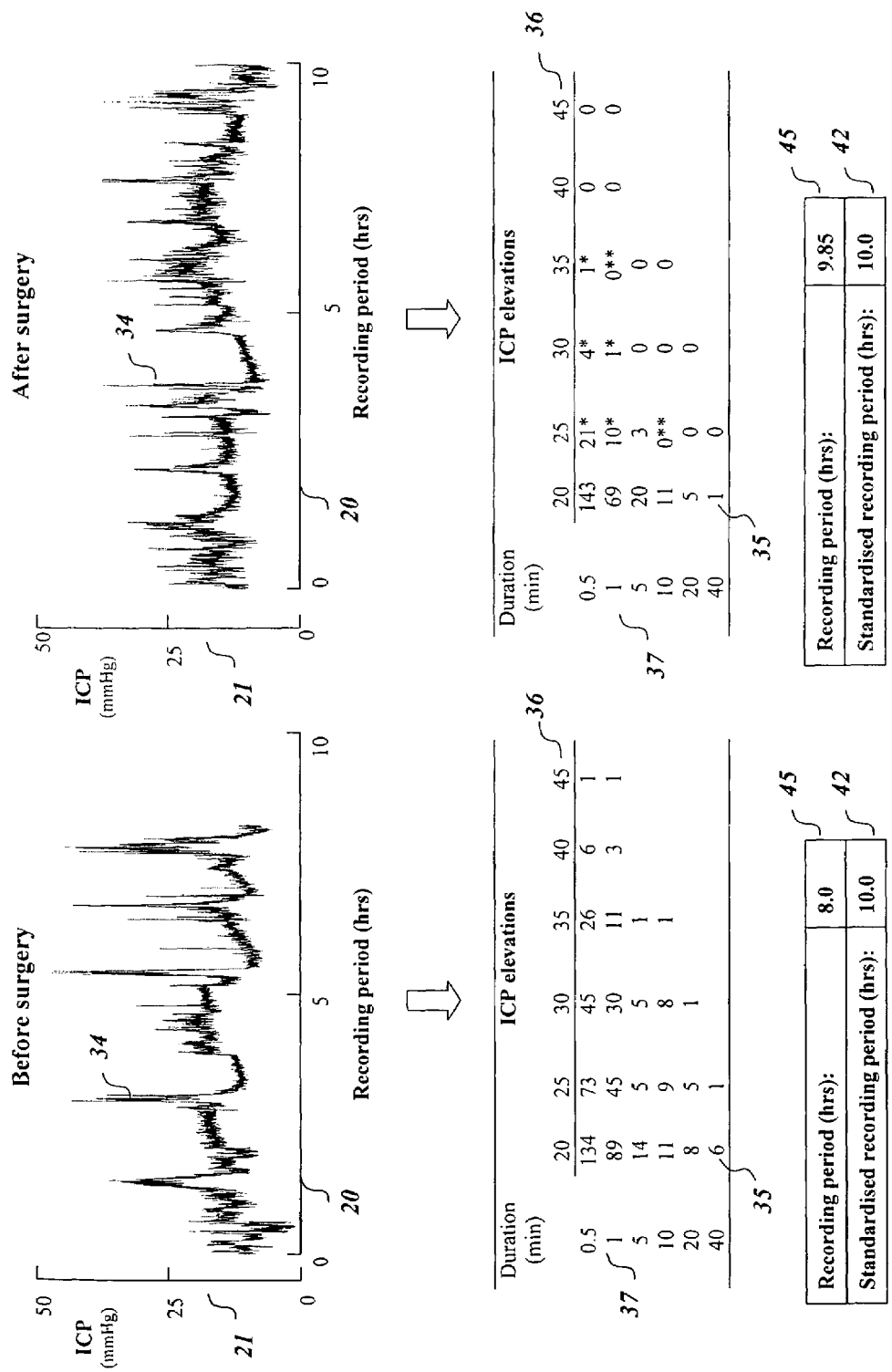
FIG. 6 is a presentation of comparisons of pressure curves within an individual.

The procedure of comparing pressure curves 34 is further illustrated in FIG. 6. The pressure curves before (left) and after (right) surgery are shown, and below the matrix 35 of numbers of pressure elevations. The numbers are standardized to a 10 hrs recording period 42. More details are given in Example 2 below. This example is intended to illustrate various aspects of the invention described in FIGS. 2-6, but is not intended to limit the scope thereof.

EXAMPLE 2

Continuous intracranial pressure monitoring was performed in a 3 years and 10 months old boy due to suspected premature closure of the cranial sutures. The boy had symptoms of increased intracranial pressure. During sleep the data of the intracranial pressure curve were as follows: Mean intracranial pressure 15.4 mmHg, range 0-57.1 mmHg, std 6.0 mmHg, and time of pressure recording 480 min (8.0 hrs). On the basis of the results of intracranial pressure monitoring, surgery was performed. A cranial expansion procedure that is a rather major procedure was performed to increase the cranial volume and thereby reduce intracranial pressure. However, after surgery the patient still had symptoms of intracranial hypertension. Therefore it was decided to repeat the intracranial pressure monitoring, that was undertaken six months after surgery. The data for this monitoring during sleep were as follows: Mean intracranial pressure 15.2 mmHg, range 5.5-39.4 mmHg, std 3.9 mmHg, and time of intracranial pressure recording 591 min (9.85 hrs). This new intracranial pressure monitoring was inconclusive because mean intracranial pressure was unchanged after surgery. In retrospect, the monitoring of intracranial pressure was without purpose since no conclusions could be drawn on the basis of the pressure recordings. Though the pressure was unchanged after surgery, it was decided not to perform a new operation though the results of intracranial pressure monitoring did not document any reduction of intracranial pressure after cranial expansion surgery. A "wait and see" policy was chosen on the basis of intracranial pressure monitoring. However, when the method according to the present invention was applied retrospectively to the intracranial pressure curves before and after surgery, it was found a marked and significant reduction of number of intracranial pressure elevations. The matrix 35 of numbers of intracranial pressure elevations of different levels 36 and duration's 37 before and after surgery is presented in both Table 1 and FIG. 6. In FIG. 6 both the intracranial pressure curve and the corresponding matrix 35 of intracranial pressure elevations of different levels 36 (20-45 mmHg) and durations 37 (0.5-40 minutes) are presented (before surgery at left and after surgery at right). The matrix 35 is presented as numbers during a standardised recording time of 10 hours 42 (actual recording time 45 before surgery 8 hours and after surgery 9.85 hours). The results documents that surgery had a major effect in reducing the number of intracranial pressure elevations despite an unchanged mean intracranial pressure. After surgery, there were no elevations of 40 or 45 mmHg, the number of elevations of 25, 30 or 35 mmHg were markedly and significantly reduced, whereas the number of intracranial pressure elevations of 20 mmHg were not significantly changed. For example, during a standardized recording time of 10 hours, intracranial pressure elevations of 30 mmHg lasting 1 minute occurred 30 times before surgery (left matrix) and one time after surgery (right matrix). Various statistical methods may be applied to the data to identify statistically significant changes. Accordingly application of this method would have justified no re-operation in a stronger and more reliable way. The patient has been followed for an observation period of 2 years without surgery and has shown a satisfactory development in this period.

As can be seen from the above mentioned examples the invention provides an accurate way of comparing pressure curves. The standardization procedure is crucial. For example it may be useful to compare pressures during sleep. The recording periods may be different, therefore it may be useful to standardize to a given recording time. It might not be representative to for example select one of 6 hours of recording.

In FIGS. 2-6 changes in the pressure curves of longer duration (30 seconds or above) have been illustrated. Though reference has been made to intracranial pressure, this represents no limitation of the invention. Pressures from other body cavities may be presented in the same way.

In the following FIGS. 7-10 the invention applied to single pulse pressure waves is described. Analysis of single pulse pressure waves represents an even more detailed strategy for comparing pressures between and within individuals.

With regard to data collection, several steps are basically similar to the processes described for FIGS. 2-6. The signals from the sensor are converted to either a continuous current or voltage signal that is further processed in the apparatus 1 or modifications thereof. The continuous current or voltage signals are converted to digital signals within the analogue to digital converter. Another approach is to collect data from a vital signs monitor. Different from the data presented in FIGS. 2-6 a higher sampling rate is required for analysis of single waves. With regard to single wave analysis the crucial point is to have a sufficient sample rate, as well as sufficient resolution order to reproduce the pressure waveform properly. According to the experience of the inventor so far a sampling rate of at least 100 Hz is sufficient to find maximum and minimum values an calculate latency, amplitude and rise time for the first peak (P1) (see FIG. 7). A higher sampling rate (at least 200 Hz) is required to compute the latencies and amplitudes of the second (P2) and third (P3) peaks. It is required that the analogue to digital converter has a resolution of at least 12 bits. It is preferably to use 16 bits or higher.

Figure 7:
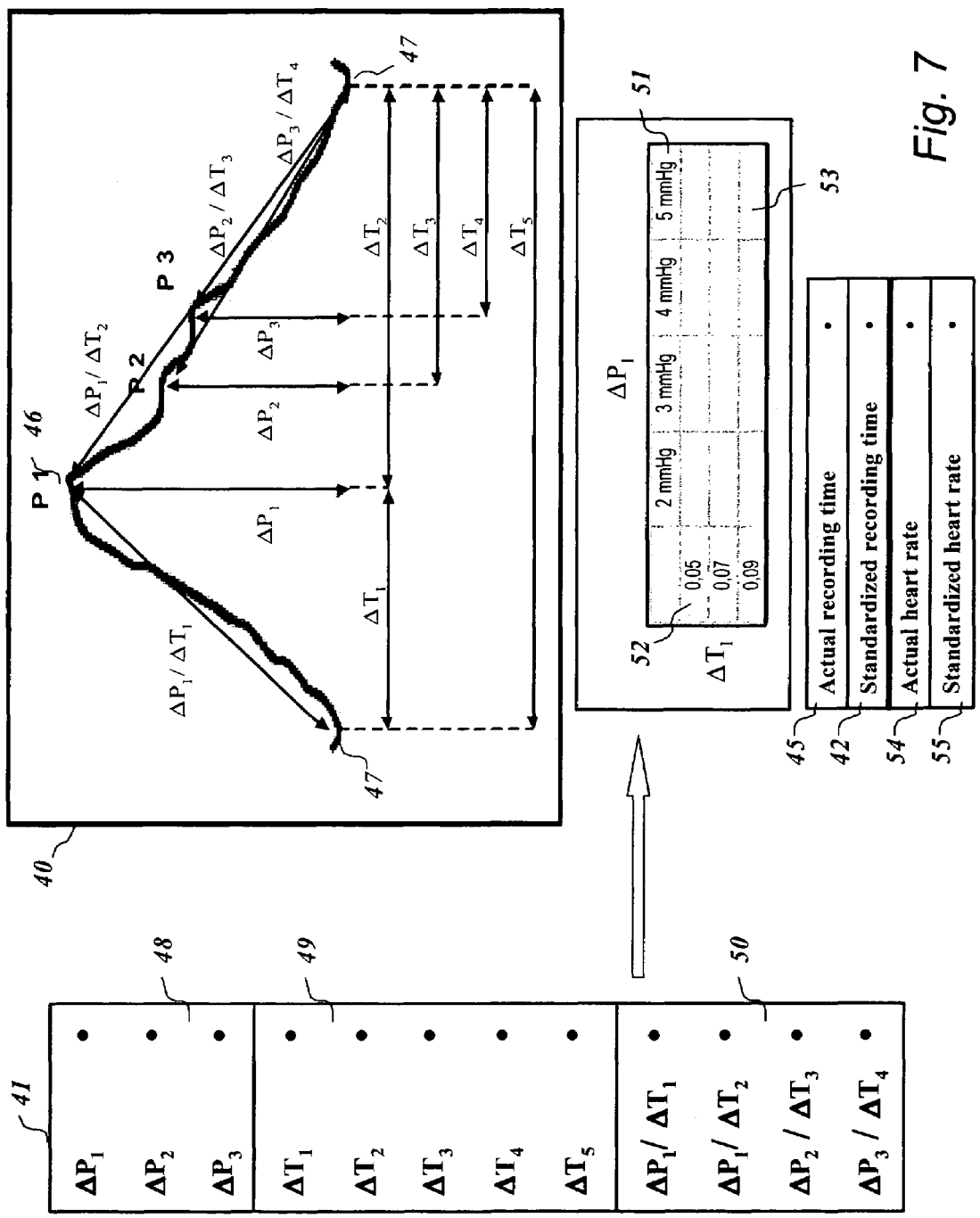
FIG. 7 is a presentation of the parameters measured during analysis of single pulse pressure waves.

Reference now is given to FIG. 7, demonstrating the parameters of a single pulse pressure wave that are analyzed quantitatively. All pressure signals are recorded, usually with a recording frequency of 100 Hz or above. The window with single pulse pressure waves is opened by pressing button 40 (FIG. 3). The single waves are defined by the maximum 46 and minimum 47 values. By pressing another button 41 (FIG. 3), the following parameters at any point on the single pressure curve may be computed: Amplitude 48, latency 49, and rise time 50.

Latency 47 represents the time interval during which the pressure is changed from one pressure to another pressure. Each pressure signal may be identified on the time scale because pressures are recorded along with a time reference. The maximum 46 and minimum values 47 identify each single wave. The latency from one minimum 47 value back to another minimum 47 value is the heart rate and the duration of the wave. The latency from minimum 47 to maximum 46 is the time where the pressure of the single wave increases from the diastolic to the systolic pressure.

People skilled in the art would know that a single intracranial pressure wave contains three peaks, the first (P1), second (P2) and third (P3). The second peak (P2) also is termed the tidal wave and the third peak (P3) the dichrotic wave. Whether the waveform is reproduced properly or not depends on a sufficient resolution order and a sufficient sampling rate. The expressions amplitude 48, latency 49 and rise time 50 are with reference to each of these peaks. The identification of the first peak (P1) is relative to maximum 46 and minimum 47. The identification of the second peak (P2) also is relative to the first peak (P1), and the third peak (P3) is relative to the second peak (P2). In the present embodiment focus is given to amplitude, latency and rise time related to the first peak (P1), though this does not represent any limitation of the scope of the invention. References may also be to the second (P2) and third peaks (P3).

For the first peak (P1), the amplitude $\Delta P1$ represents the relative pressure difference between the diastolic minimum 47 and systolic maximum 46 pressures. Latency $\Delta T1$ is the time interval by which pressures increase from diastolic minimum 47 to systolic maximum 46. Rise time $\Delta P1/\Delta T1$ is the quotient between difference in pressure divided by difference in time. The differences of pressures and time represent relative values. Any type of relationship may be calculated. The software allows the calculation of a matrix 53 of number of single pulse pressure waves with pre-selected wave characteristics of different amplitude 51 and latency 52. Any kind of combinations of single wave parameters may be computed within the matrix 53. The amplitudes 51 usually are expressed in mmHg and the durations 52 in seconds.

The results may be presented as absolute numbers or as percentages, and the results may be standardized to a selected recording time (for example each one minute, one hour, or even 10 hours recording time) 42, as compared to the actual recording period 45. During the standardisation procedure, the numbers or percentages of single waves with selected parameters are adjusted to a factor. The normalised time may be chosen in each individual. An example is given. If the actual recording time is 6 hours, and it is desired to standardise to 5 minutes recording time, the function implies that all numbers of single waves are divided with a factor equal to (6×60)/5 (that is 72.0).

Calculation of single pulse pressure waves automatically gives the heart rate because each intracranial single pulse pressure wave is built up from the blood pressure wave. Therefore the numbers of single waves with certain characteristics during a given recording time also may be standardized to a given heart rate 55, as compared to the actual heart rate 54. During the procedure of standardisation to a given heart rate, the heart rate must be selected beforehand. The recording interval also has to be selected, when an average of the heart rate must be computed. An example is given, though this is not intended to limit the scope of the invention. It is chosen to standardise the numbers or percentages of certain single waves to a heart rate of 60 beats a minute. Furthermore, it is chosen to average the heart rate to each 5-second recording period. During this recording period of 5 seconds the averaged heart rate is computed. Given that the total continuous recording period is 6 hours this standardisation analysis has to be repeated a total of 4320 times (×12/minute, ×720/hour). Given that the actual average heart rate is 120 beats a second in a 5 seconds interval, the numbers or percentages of single waves during the period of 5 seconds must be divided by 2, to be standardised to a average heart rate of 60 beats a second. On the other hand, if the average heart rate is 30 during the 5 seconds interval the numbers or percentages of single waves during these 5 seconds has to be multiplied with a factor of 2, to be standardised to a heart rate of 60 beats a second. This approach also allows for on-line and real-time update of standardised numbers or percentages to a given heart rate since such an update may be performed repeatedly every 5 seconds.

With regard to presentation of single wave parameters, a number of variations are possible. The matrix 53 of pre-selected characteristics of amplitude 51 and latency 52, may be presented repeatedly and comparisons between matrixes 53 at different times may be performed. Only certain single wave parameters may be compared. The numbers/percentages of single wave parameters may be subject to any type of statistical analysis.

Figure 8:
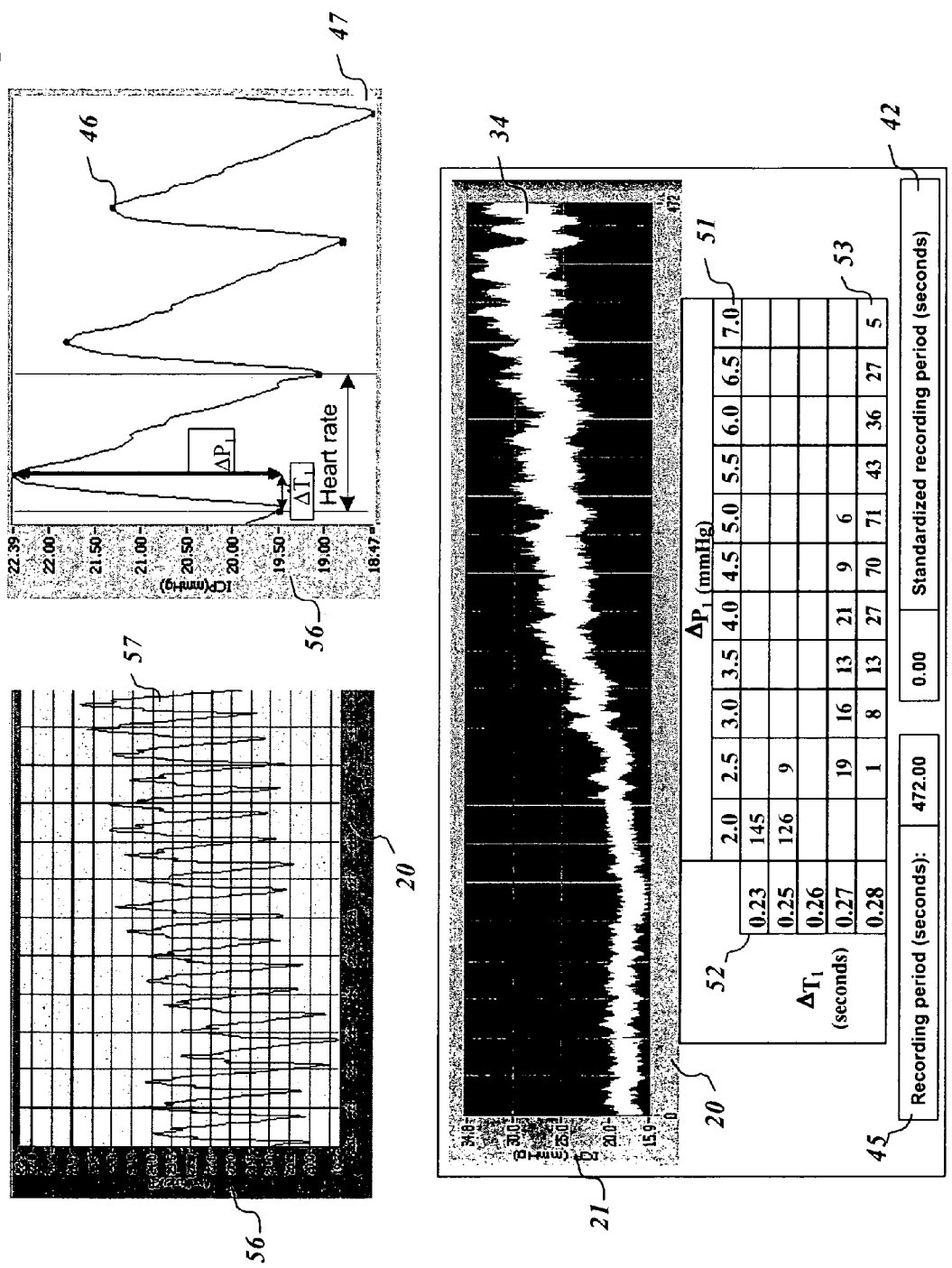
FIG. 8 is parts of graphical user interfaces for presentation of single pulse pressure waves.

FIG. 8 illustrates the computation of single pulse pressure waves with certain pre-selected characteristics. The mathematical process of quantitative analysis of single wave parameters may be implemented in the software in various ways, one strategy of implementation is described here. The acquired signal is first run through separate detection of minimum 47 and maximum 46 values. The maximum threshold value is set to the lowest level in the signal, and width greater than pre-selected seconds. A variety such pre-selected seconds may be chosen, and the values may depend on age. In the first studies, durations of 0.1-0.2 seconds were used, but other durations may also be used. The minimum threshold is set to highest signal level, and the width is set to pre-selected seconds, as described above. After this analysis all maximums 46 and minimums 47 are represented with an amplitude value and a location value or time stamp. The locations are reported in indices from the start of processing. This procedure will result in a lot artificial maximum and minimum detections. In other words the maximum 46 and minimum 47 detection has to be refined. After this is done the result is a collection of approved maximum and minimum pairs, which in the next turn can be presented to the function handling the dynamic parameter analysis. First, grouping of the maximum values and minimum values is performed. For every maximum 46 the subsequent minimum 47 is found. This couple makes a maximum-minimum pair. The latter maximum-minimum pair is inspected for threshold level. The threshold value has to be larger than a given value. This is performed by subtracting the maximum amplitude and minimum amplitude. If this value is less than the threshold value the pair is discarded. Afterwards the pair is inspected for the rise time ($\Delta P1/\Delta T1$). The rise time is expressed as maximum amplitude minus minimum amplitude divided by maximum location minus minimum location. This will remove pairs caused by for example an artefact in the collected signal. All rise time values with a value equal or larger than a given value is discarded. A large variation is possible with regard to rise times that are discarded. The collection of maximums and minimum's contained now only approved values. All the dynamic values are calculated by using the approved maximum-minimum pairs. The values which are calculated are amplitude ($\Delta P1$) (delta intracranial pressure expressed in mmHg) 51, latency ($\Delta T1$) 52, and rise time ($\Delta P1/\Delta T1$) 59, and heart rate 58. All these values are quite forward to find using the information found in the approved maximum-minimum pairs. The collections of amplitude ($\Delta P1$) 51 values give information constituting the matrix column information. The collections of latency ($\Delta T1$) values 52 give the matrix row information. A matrix 53 of different amplitude 51 and latency 52 combinations is computed.

An important aspect with the computation parameters of single pulse pressure waves is that the invention computes the relative differences in pressures and time. These relative differences are not related to a zero level of pressure. Accordingly, the single wave analysis is not influenced by the zero level of pressure, neither of drift of the zero level of the sensor. It should be noted that the procedure of calculating pressure elevations of various durations FIGS. 3-6 involves computation of absolute intracranial pressures (or other pressures in a human body cavity) relative to atmospheric pressure. The conventional methods of assessing intracranial pressure use calibration against atmospheric pressure. The present invention of computation of relative pressures of single pressure waves solves several problems of known in the art.

(a) The impact of inter-individual and intra-individual differences in pressure is reduced. When comparing continuous pressure curves between or within individuals, a source of error may be differences in the baseline pressure due to differences or drift of zero level. In the present invention, the accurate zero level does not affect the single wave parameters computed.

(b) A drift in the zero level of the pressure sensor usually is a problem with pressure sensors, particularly when pressure is monitored continuously for several days. Drift in zero level of pressure has no influence on the single wave parameters computed as described here.

(c) The major problem with continuous monitoring of intracranial pressure by means of non-invasive sensors is the problem of determining a zero level. Thereby relative differences in pressure must be computed, but the output give non-accurate data since it may be nearly impossible to suggest the intracranal pressure on the basis of such relative pressure assessments. In the present invention it has been possible to accurately compute the single waves with pre-selected characteristics of latency, amplitude and rise time. Since relative differences are computed, there is no need for a zero level. When single waves are computed by means of a non-invasive sensor, the present invention allows for determination of the intracranial pressures with a high degree of accuracy. On the basis of computing several hundred thousand of single waves and comparing the single wave parameters with the mean intracranial pressure, a high degree of correlation between amplitude, rise time and mean intracranial pressure has been found. According to this invention, single wave analysis of signals from non-invasive sensors may both give information about relative changes in pressure and about the intracranial pressure, as the relationships between intracranial pressure and single wave characteristics are known beforehand, on the basis of a large number of comparisons. This process may be as follows. A non-invasive sensor 16 may be applied to the patient and connected to the transducer 2, and the signals are processed in the apparatus 1 or modifications thereof. Such sensors 16 may use acoustic or other signals, for example by application of a sensor-device to the outer ear, sensing pressure in the middle ear indicative of the intracranial pressure. The signals are converted in the apparatus 1 and stored along with the time stamp. The computer software handles the digital signals and performs the quantitative analysis of the parameters of single pulse pressure waves described here. Without knowing the exact zero level of intracranial pressures, changes of single wave parameters may be followed continuously. This approach provides a simple approach to follow changes in intracranial pressure, and obtaining accurate information about the intracranial pressure.

(d) It is possible to implant permanently pressure sensors within the intracranial compartment, for example in conjunction with ventricular shunts. Telemetric devices may record pressures. Also with this type of pressure monitoring, drift of zero level remains a problem, hence it may be a question of whether the correct pressure is monitored. The present invention soles this problem as drift in zero level does not affect the pressures recorded.

Exploration of the single pulse pressure waves is started by pressing the button 40, and the single wave parameters are selected by pressing the button 41. The upper figures in FIG. 8 shows the single pulse pressure waves 57, including the time recordings 20 along the X axis, and pressure levels 56 along Y axis. On the Y axis the absolute pressure values are shown, it should be noted, however, that the single pulse pressure waves are calculated by computation of relative pressure and time differences. As indicated in the upper figure to the left (FIG. 8), the single waves are identified by the minimum 47 and maximum 46 values. For the first peak (P1), the amplitude (ΔP1) and latency (ΔT1) are both indicated.

In FIG. 8 is also indicated the process of computing numbers of characteristics of single pulse pressure waves. A graphical user interface reveals the curve of intracranial pressure 34. A window revealing the pressure curve 34 along with the absolute intracranial pressure recordings 21 and the time of registration 20 is shown. The actual recording period 45 was 472.0 seconds, and the recording period was not standardised 42 (0.00 in output box). During this period of recording the numbers of single pulse pressure waves with pre-selected characteristics where computed. The amplitudes of single waves 51 were selected to either 2.0, 2.5, 3.0, 3.5, 4.0, 4.5, 5.0, 5.5, 6.0, 6.5 or 7.0 mmHg. The latencies of the single waves 52 were either selected to 0.23, 0.25, 0.26, 0.27, or 0.28 seconds. The numbers of single pulse pressure waves with these pre-selected characteristics were computed and presented in the matrix 53. For example, during the recording period of 472.0 seconds, single pulse pressure waves with an amplitude of 5.5 mmHg and a latency 0.28 seconds (that is rise time of 5.5/0.28=19.64 mmHg/sec) occurred 43 times during this recording period. The results may be standardized 42 to a recording time of for example 600 seconds. In this situation all numbers must be multiplied with a factor of 600/472. The numbers also may be standardised to a selected heart rate, as described above. A number of variations are possible with regard to methods of data presentation.

The invention provides the option for comparisons of pressure curves. For example, during monitoring of intracranial pressure during sleep the numbers of single waves with certain pre-selected characteristics may be computed (for example amplitude 4 to 8 mmHg and latency 0.25-0.28 seconds). The numbers of such single waves may be computed during a standardized recording period (e.g. each one minute or each one hour) and a standardized heart rate (e.g. 70/min). The numbers of single waves may be computed within the same individual at different times (e.g. before and after treatment) and compared. Alternatively the numbers of single waves may be computed within an individual and the numbers may be compared against a normal material.

Figure 9:
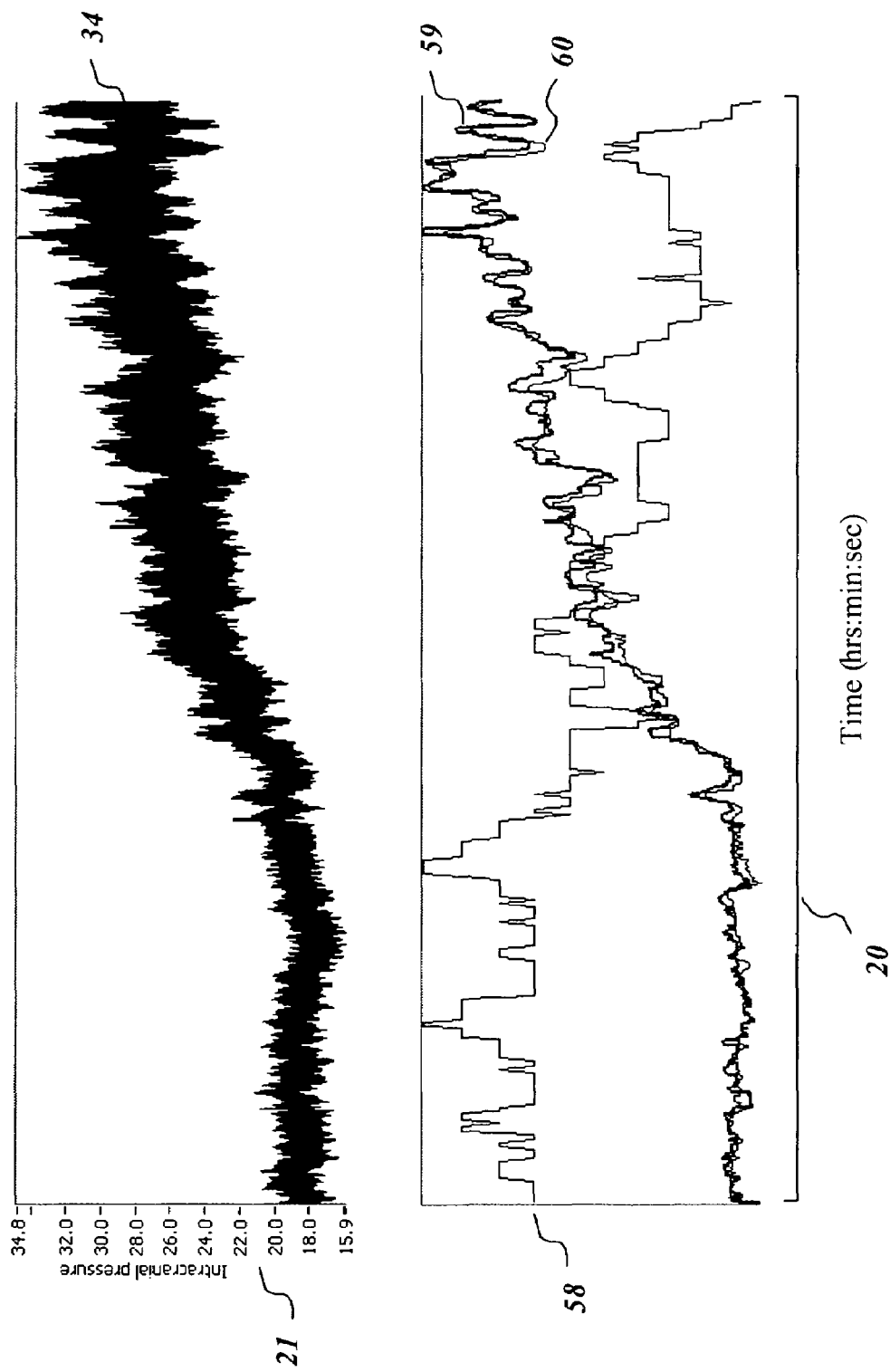
FIG. 9 is graphical user interfaces for presentation of pressure recordings and parameters of single pulse pressure waves during an infusion test.

FIG. 9 demonstrates the recordings of intracranial pressure (cerebrospinal fluid which represent one of the compartments of the intracranial cavity) 34 while infusing a liquid into the cerebrospinal space. Pressures are presented as absolute values of mmHg on the Y axis 21 and time is expressed as seconds on the X axis 20. The intracranial pressure 34 is measured simultaneously with infusion of physiological saline into the lumbar cerebrospinal space, which is termed infusion test. It is shown how the intracranial pressure curve 34 increases as liquid is infused. The increase of pressure is shown in the upper figure. The figure also demonstrates the simultaneous computation of rise time 59-60 and heart rate 58. With regard to rise time, two parameters are computed simultaneously, namely ΔP1/ΔT1 59 and ΔP1/ΔT2 60. It is shown that the rise times ΔA1/ΔT1 59 and ΔP1/ΔT2 60 increase with time. The heart rate 53, on the other hand, declines as the pressure increases. This illustrates that the rise times may be calculated repeatedly and plotted against time (X-axis). Alarm functions may be incorporated for example alarming the occurrence of ΔP1/ΔT1 59 above a given level. Rise time may be an important predictor of abnormal pressure. The present technical solution allows for computation of the exact numbers or percentages of single waves with certain rise times during a given recording time. For example, the numbers or percentages of single waves with a rise time between for example 10 and 30 mmHg/seconds during 5 minutes of recording may be computed repeatedly, and presented graphically. FIG. 9 shows some examples of presentation of single wave characteristics, though the examples represent no limitation of the scope It should be noted in FIG. 9 that heart rate declines as the rise time increases. This is a physiological effect in the way that heart rate declines as a result of increased decompensation related to increased pressure. Since the relative duration of each single wave corresponds to the heart rate, the heart rate may be automatically computed. The observation presented in FIG. 9 further illustrates the value of concomitant recording of heart rate. The parameter heart rate provides additional information about abnormality of intracranial pressure.

Figure 10:
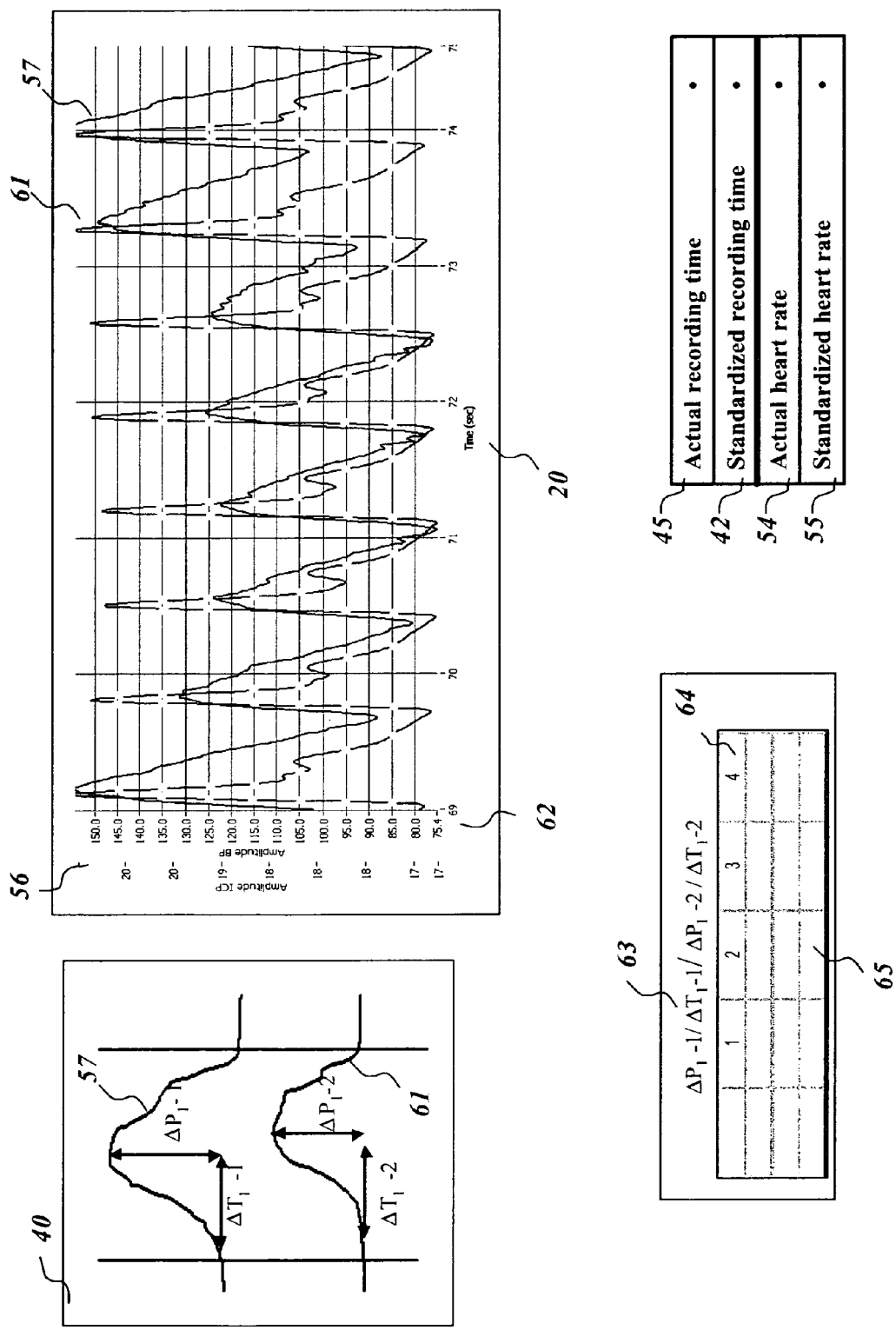
FIG. 10 is a presentation of comparisons of parameters of different types of single pulse pressure waves.

FIG. 10 shows strategies to compare pressure curves. The input box 40 (FIG. 3) allows for comparisons of various single pulse pressure waves. In particular single pulse pressure waves of intracranial pressure and blood pressure may be compared, but any type of pressure may be compared. The different pressure waves are revealed simultaneously during real time on-line monitoring, with the identical time reference. The output may be time on the X axis 20 and pressure 21 on the Y axis. For example, the curve of single arterial blood pressure waves 61 may be revealed simultaneously with the single intracranial pulse pressure waves 57. For a given recording period 45 the numbers of single pulse pressure waves may be computed and the numbers may be standardised to a given recording period 42. Furthermore the actual heart rate 54 may be standardised to a standardised heart rate 55. The curves of single pulse intracranial 57 and arterial blood pressure 61 waves are presented in the upper figure to the right. The time reference 20 is identical, thus allowing comparisons of single pulse pressure waves at identical points of time. The Y axis reveals the absolute blood pressure 62 and intracranial pressure 56 values. As described for intracranial pressure, a matrix may be computed with the opportunity to define relationships between parameters of different single waves. In the lower figure to the left is shown a matrix 65 defining numbers of relationships between rise time for intracranial pressure waves ($\Delta P_1$-1/$\Delta T_1$-1) and rise time of blood pressure waves ($\Delta P_1$-2/$\Delta T_1$-2). This relationship ($\Delta P_1$-1/$\Delta T_1$-1)/($\Delta P_1$-2/$\Delta T_1$-2) has been computed and the matrix 65 presents the numbers by which this relationship was 1, 2, 3, or 4. This example represents no limitation concerning the relationships between single waves that may be computed.

The computer software may be integrated in the portable apparatus 1, as well as in a network station, a personal computer, medical device computers 6, computer servers 6 connected to vital signs monitors, or incorporated directly in vital signs monitors. Output from the quantitative analyzes may be presented on the monitor screen, flat screen or other devices known in the art.

FIG. 11 illustrates graphical presentations of pressure curves 34, with accompanying matrix 53 with single wave characteristics such as amplitude 51 and latency 52. To the left is presented the pressure curves of intracranial pressure from three different patients (cases A-C). For each pressure curve is shown the continuous pressure recordings 34, along with the time of registration 20 and the absolute pressures 21 on the Y-axis. To the right for each pressure curve 34 is shown a histogram presentation 66 of the matrix 53 with pressure amplitudes 51 and latencies 52. For each individual case the matrix 53 including amplitudes 51 and latencies 52, was standardised to a standardised recording period 42 and a standardised heart rate 55. For each case (A-C), the standardised recording period 42 was set to one hour. The actual recording time 45 was 6 ½ hours (11:30-18:00) for case A, 10 hours (21:00-07:00) for case B, and 10 hours (22:00-08:00) for case C. The actual heart rate 54 varied between these cases, but was standardised to a standardised heart rate 55 of 70 beats a minute in all three cases. The resulting matrix 53 of numbers of single waves with certain amplitudes 51 and latencies 52 is presented in histograms 66. On the Y axis 67 is shown percentage of occurrence that is how often a single wave with a combination of a certain latency 52 and amplitude 51 occurred in percentage of the total number of single waves during the recording period. On the X-axis 68 are shown the different combinations of latency 52 and amplitude 51. For example, in these histograms, the label 0.14|8.50 on the X-axis refers to single waves with latency 52 ($\Delta T_1$) of 0.14 seconds and amplitude 51 ($\Delta P_1$) of 8.50 mmHg. Accordingly, the bar 69 corresponding to the label 0.14|8.50 shows the percentage of single waves with this combination occurring as percentage of total number of single waves during a standardised recording time of 1 hour and a standardised heart rate of 70 beats a minute. This type of histogram presentation of distribution of single waves provides fundamentally new description of pressure curves. The pressure curve of case A is abnormal after current criteria. Mean intracranial pressure for the whole period is 19.8 mmHg. The corresponding histogram of single wave distribution to the left show a right orientation of the bars 69, that is a large proportion of single waves with high amplitudes 51. In case B, on the other hand, the pressure curve is completely normal according to current criteria, mean intracranial pressure for the period is 3.96 mmHg. The corresponding histogram 66 of single wave distribution, on the other hand, shows a right-orientation similar to that in case A. Accordingly, abnormal frequency of single waves was present despite a normal pressure curve according to current criteria. In case C, the pressure curve revealed a higher pressure (mean intracranial pressure 7.4 mmHg), as compared to case B (mean intracranial pressure 4.0 mmHg). However, in case C, the single wave distribution was left orientated, with single waves with low amplitude. For example, in case C the combination on the X-axis of 0.17|2.00 (i.e. single waves with latency 52 ($\Delta T_1$) of 0.17 seconds and amplitude 51 ($\Delta P_1$) of 2.0 mmHg) was common, but not observed in case B. The combination on the X-axis of 0.21|10.00 (i.e. single waves with latency 52 ($\Delta T_1$) of 0.21 seconds and amplitude 51 ($\Delta P_1$) of 10.0 mmHg) was not observed in case C, but was frequent in case B. The matrix 53 or histogram 66 may be subject to further mathematical analysis to determine the centroid (or centroidial axis) or centre of mass of the single wave combinations of latency and amplitude.

Such histograms may be made after the end of pressure monitoring that is off-line. This represents no limitation of the invention as histograms may be computed real-time and on-line repeatedly. For example, histogram presentation may be computed repeatedly each 5 or 10 seconds or each one minute, with or without standardisation functions. Such histograms may be incorporated in patient monitors with bars to the right indicated by red and bars to the left indicated as blue, to incorporate alarm functions. When single wave distribution changes to the right (i.e. amplitudes of single waves increase), actions should be taken to reduce pressure.

Instead of presenting the histograms, the balanced position of single wave combinations of latency/amplitude such as centroidial axis or centre of mass may be computed and displayed. Updates each 5 second represents an alternative to the conventional strategy of computing the average of pressure signals during for instance a 5 second interval.

Though examples are given concerning intracranial pressure, similar functions may be made for any type of pressure (blood pressure, cerebral perfusion pressure, cerebrospinal fluid pressure etc.). Which types of single wave distribution that should be considered as abnormal depends on type of pressure.

Figure 12:
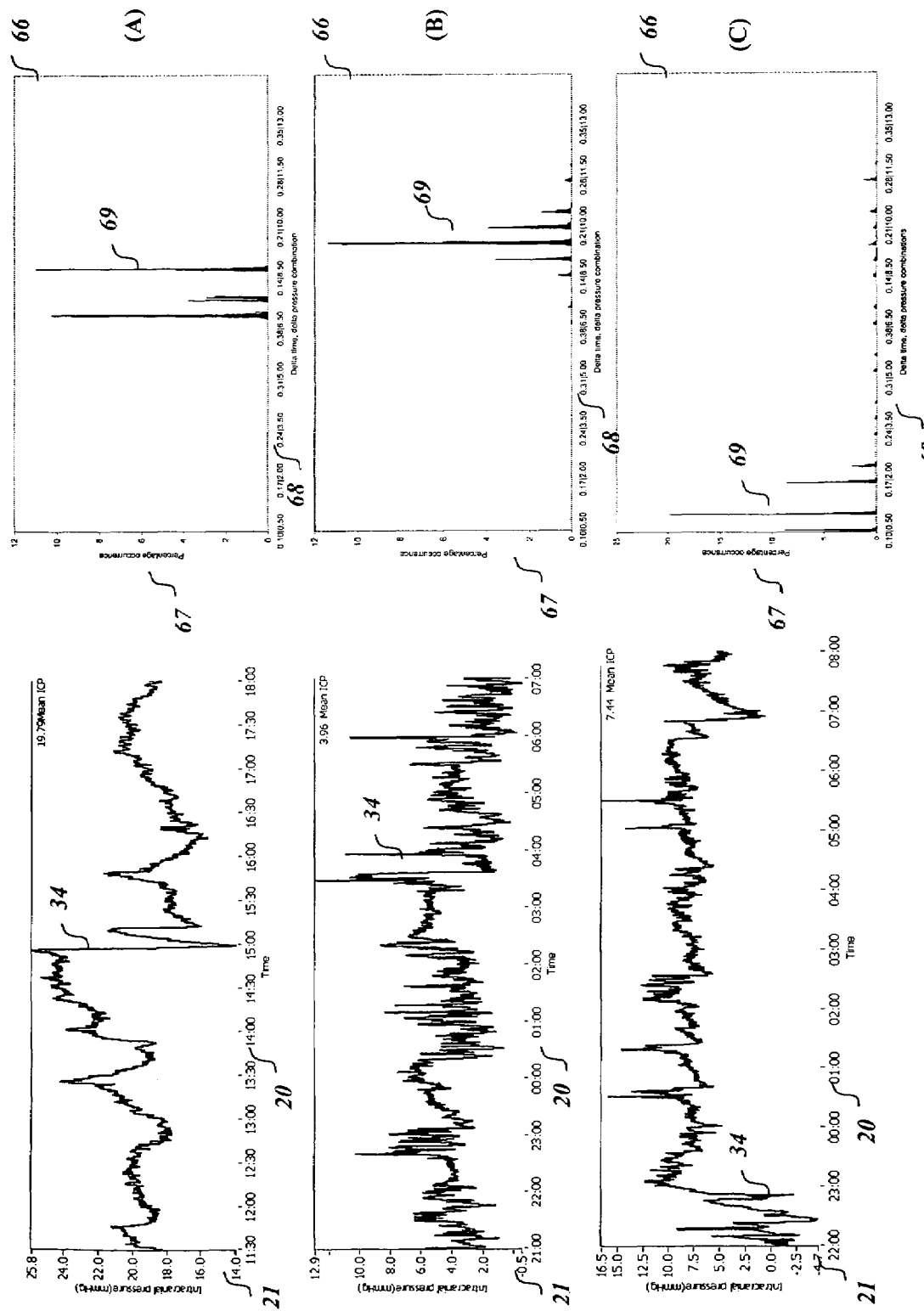
FIG. 12 presents the pressure curves and the accompanying histograms of single wave distribution for simultaneous intracranial pressure recordings via both intraparenchymatous and epidural sensors.

References now are given to FIG. 12, showing two different intracranial pressure recordings in one single case. Pressures were recorded simultaneously by means of one sensor placed within the brain parenchyma (upper curve and histogram—A) and one sensor placed epidurally (lower curve and histogram—B). An epidural placement means that the sensor is placed outside the dura mater, actually mimicking non-invasive pressure monitoring since the sensor is not placed within the cavity in which pressure is measured. For both pressure curves 34 are presented the absolute pressures 21 on the Y-axis and the time of recording 20 on the X-axis. It should be noted that the absolute pressures differ markedly for the pressure curve for parenchymatous (A) and epidural (B) pressures. For the upper curve (A) mean intracranial pressure was 8.9 mmHg and for the lower curve (B) mean intracranial pressure was 10.3 mmHg. The morphology of the curves also was markedly different. On the other hand, the distribution of single waves was nearly identical between intraparenchymatous (A) and epidural (B) measurements. The histogram 66 is a graphical presentation of the matrix 53 of amplitudes 51 and latencies 52 of single waves, where the actual recording time 45 of 6 hours (22:00-04:00) is standardised to a standardised recording time 42 of 1 hour, and the actual heart rate 54 is standardised to a standardised heart rate 55 of 70 beats a minute. The histogram 66 shows on the Y-axis the percentage occurrence, which is how often a single wave with certain characteristics occurs in percentage of the total number of single waves during the recording period. On the X-axis is the matrix combination. For example the label on the X-axis of 0.38|6.50 refers to single waves with latency 52 of 0.38 seconds and amplitude 51 of 6.50 mmHg. For intraparenchymatous (A) and epidural (B) pressures, the single wave distribution is nearly identical. These figures illustrate the following: Continuous pressure recordings are most accurately described by the single wave distribution. Single wave distribution may be similarly presented whether or not the sensor is placed within the cavity pressure is measured.

The invention may not exclusively be used in humans but may as well be used in animals, both in the clinical practice and in scientific experiments.

The invention is intended used in several groups of patients with various clinical problems. Some examples are given though these should not be understood as limitations of the scope of the invention.

Continuous intracranial or cerebrospinal fluid pressure monitoring according to the invention described here may be used in adults and children. (a) In children intracranial hypertension may be questioned on the basis of hydrocephalus, craniosynostosis, pseudo-tumor cerebri and questions of. (b) In children and adults either intracranial hypo- or hypertension may be questioned on the basis of shunt failure. (c) In adults with questions of so-called normal pressure hydrocephalus intrcaranial hypertension or abnormal absorption of cerebrospinal fluid may be questioned. (d) In individuals in the intensive care unit, a vital aspect is to follow abnormal changes in intracranial and blood pressures.

Continuous blood pressure monitoring according to present invention may be used in (a) assessment of blood pressure medications, and in (b) children and adults in the intensive care unit in whom continuous blood pressure monitoring is used as part of the patient monitoring.

Though focus is given to intracranial pressure (including cerebrospinal fluid pressure), blood pressure, and cerebral perfusion pressure, any type of pressure in a human body cavity may be assessed according to the invention described here.

The pressure transducer may be connected directly to the vital signs patient monitor and the pressure signals may be transferred via a network solution to another server or to personal computers. Alternatively, modifications of the apparatus may be used as an interface between the pressure transducer and the computer. Though an invasive method of recording pressures is described here various types of non-invasive sensors may be used.

When pressures are measured in the cerebrospinal fluid during so-called infusion testing, a catheter is applied to the cerebrospinal fluid space, usually either within the cerebral ventricles or to the lumbar cerebrospinal fluid space. The catheter is connected to a commercially available sensor for sensing pressures within a liquid. This pressure sensor 16 may be connected via the apparatus 1 described here to a commercially available computer, or via a vital signs monitor to the computer. In this situation the apparatus 1 is modified, thus serving as an interface between the sensor and the computer. Pressure recordings are made while a fluid is infused to the cerebrospinal fluid space. The applicant has shown that recordings of single pulse pressure waves may be done simultaneously as the fluid is infused. According to this intervention the various parameters of the single pulse pressure waves may be calculated as well as the heart rate variability during infusion of liquid. Various strategies of assessing single pulse pressure waves may be performed in this situation. The distribution of single waves during one minute of recording may be computed and related to the volume change that is known in this situation. The invention allows for standardisation of numbers or percentages to a given heart rate and a given recording period. For example, the matrix 53 of single waves with various amplitudes 51 and latencies 52 may be computed repeatedly during one minute of recording. Since the infusion rate and hence volume change is known a curve for each individual may be computed with percentage of pre-selected single wave on Y axis and volume change on X axis. When the curves of many individuals are known it is also possible to superimpose the recordings from one individual against a reference curve from several individuals. It has previously not been possible to superimpose the intracranial pressure recordings of a single subject on the pressure volume or elastance curve. The present invention may provide a technical solution for this problem. Since any types of single pulse wave parameters may be calculated by this invention, a variety of approaches may be possible.

With regard to on-line presentations, pressures (for example intracranial and blood pressures) may be presented by conventional means as real-time presentation of numerical values of mean pressure or as real-time presentations of intracranial pressure curves. The present invention provides a technical solution for continuous analysis and presentation of parameters of single pulse pressure waves. For example, the numbers or percentages of a certain rise times (for example 10-20 mmHg/sec) during a given recording period (e.g. 1 minute) may be computed repeatedly and presented on a graph. Thereby changes in pressures may be detected before the conventional methods, thus providing early detection/warning of deterioration of pressures.

The invention also may be use to compare changes in blood pressure before and after interventions. Comparable to the situation described for intracranial pressure quantitative analysis and presentation of continuous blood pressures may be computed. Changes in numbers or percentages of single pulse pressure wave parameters may be compared. In the assessment of treatment of blood pressure, comparison of pressure curves before and after treatment is of interest. Single pulse pressure wave parameters may be calculated before and after treatment with blood pressure medications. The invention provides a detailed approach for assessment of these treatments. It should be noted that the invention may both be used in clinical practice and in scientific practice. Pressure may be monitored in both humans and animals. In particular, the invention may be used in animal experiments in which blood pressure medications are assessed.

This invention represents a new technical solution in various aspects, which now will be commented on:

(a) The invention provides a technical solution for digital recording of pressures in individuals that are free to move about.

(b) The present apparatus allows for digital storing of a large number of intracranial and blood pressure recordings, different from the currently available apparatuses.

(c) The standardisation procedure described here makes it possible to compare curves of different individuals, though the recording time for each individual may be different. Without this standardisation procedure, an alternative strategy might be to select pressure curves of identical duration from different individuals. Then it would be required to select one part of the curve; however, then it might be difficult to select a representative part of the curve. For example, if intracranial pressure or blood pressure is recorded continuously in one individual twice (one recording of 7 hours and one recording of 9 hours) and the two recordings are going to be compared, the problem is to compare representative portions of the curves. The present invention provides a technical solution to this problem by means of standardising the recordings to a given recording period. Thereby the whole recording period may be utilised in the assessment.

(d) Though a major use with the present invention is off-line assessment of pressure recordings, the invention may as well be used for on-line and real-time monitoring of single pulse pressure waves (blood pressure, intracranial pressure, cerebral perfusion pressure, or other pressures in a human body cavity). The invention provides a technical solution for continuous calculation and presentation of single pulse pressure characteristics. Calculation of the accurate numbers or percentages of single pulse pressure parameters and comparisons of these parameters at different times, provide a technical solution for early detection/warning of changes in pressure. An example is given. The present invention allows for calculation of the exact numbers or percentages of single pulse pressure waves with amplitude 6 mmHg and latency 0.23 seconds (rise time 26 mmHg/sec) during one minute or 5 minute recordings. Given that the presence of 60% of such waves during a given recording period represents abnormality, it would be informative for the physician to have a graphical presentation of repeated computations of the percentage of this single pulse pressure wave. In fact, the invention allows for repeated computations of any combinations of single pulse wave parameters. A continuous and real time computation of the numbers or percentages of certain rise times (for example 26 mmHg/sec) during a given recording period represents an alternative presentation. Accordingly, this invention provides a technical solution for early warning of deterioration of pressures.

(e) The quantitative algorithms and methods of assessing pressures have previously not been described. Several authors have used methods to explore the frequency distribution of pressure waves. In particular spectral analysis or Fast Fourier Transformation (or spectral analysis) has been used. These methods are fundamentally different from the methods described here.

(f) The invention provides a technical solution for monitoring intracranial pressure without the problem of zero drift of pressure sensors or the problem of identifying the zero level. The quantitative method of analysing single pulse pressure waves utilises relative changes in pressures and time, and therefore not is dependent on the zero level of pressures. It is well known that drift of zero level of a pressure sensor represents a methodological problem, in particular with invasive sensors. When continuous monitoring is performed over time such as several days, drift of the zero level of the sensor may produce false pressure recordings. This is related to the fact that such sensors are calibrated against the atmospheric pressure. The same problem is seen with pressure sensors that are permanently implanted, for example implanted with a cerebral ventricular shunt system. These sensors may for example give a radio frequency signal that is recorded by a telemetric device. The present invention of signal handling eliminates the problem of zero drift. With regard to non-invasive sensors the problem is to define a zero level. For intracranial pressure, the establishment of a zero level requires calibration against the atmospheric pressure. The present invention computes the relative changes of single wave parameters. In this situation the zero level of pressure may not be known. By means of the present invention changes in parameters of single pulse pressure waves may be followed over time without the need for adjustment of zero level.

(g) The present invention provides a technical solution for comparisons of pressure curves within a body cavity, that is comparisons of waves in a wide sense of the word. Examples are comparisons of continuous pressure recordings within a single subject at different times, such as comparisons during a continuous monitoring of pressures. Alternatively continuous pressure recordings may be compared at different times, such as before and after treatment. Pressure curves may be compared between individuals or continuous pressure curves from an individual may be compared against a reference material. For example, continuous intracranial pressure is monitored for 12 hours in a single subject. The numbers of single pulse pressure waves with pre-selected characteristics concerning latency and rise time are computed. Since selection of only one portion of the curve would reduce the accuracy of the recordings, the numbers or percentages of the whole recording period may be standardised to a selected recording period. For example, the numbers or percentages of single waves with certain amplitudes and latencies during the actual recording period of 12 hours may be standardised to numbers of waves during one hour of recordings. This approach takes away the inaccuracy of selecting only one portion of the curve. In addition to computing the quantitative characteristics of high frequency fluctuations in pressure, quantitative analysis of the low frequency fluctuations in pressure may be computed, providing a more complete picture of the pressures. For low frequency pressure changes the normal distribution of pressure elevations of 20 mmHg lasting 10 minutes during for example one hour of recording may be computed. Due to some individual variation in the normal distribution exact values may not be computed but rather a distribution with the median and percentile distribution.

(h) The invention provides a new technical solution for the clinical application of single wave analysis, when assessing continuous pressure recordings. Single pulse pressure wave parameters are calculated quantitatively, and the numbers or percentages of certain single waves may be computed. The numbers/percentages may be computed during a given recording period. Thereby the invention provides the unique opportunity to predict the placement of a continuous pressure recording in one individual on the elastance or pressure-volume curve. It has previously not been possible to superimpose the pressure recordings of an individual on the pressure-volume (elastance) curve because this curve is different for different individuals and the curve may vary over time. The effect of this inter- and intra-individual variation is markedly reduced by the present intervention. The present intervention provides a tool for computing a diagram of the normal variation of the pressure volume curve. For example the exponential pressure volume curve originally described by Langfitt in 1966 (volume on the X axis and pressure on the Y axis) may be presented as medians with percentiles. The present invention provides a tool for computing the distribution of certain single pulse pressure waves that may be considered as abnormal. For example, given that it is found that the presence of a single wave with amplitude 6 mmHg and latency 0.23 seconds in 60% of the recording time is abnormal, the invention provides the option to compute in a single patient the numbers and frequency of such single waves. During infusion testing pressure changes are known along with changes in volume because the rate of volume change is known. This situation provides the opportunity to compute the distribution of the different waves at different levels of the curve. For example, the distribution of a single wave with a rise time 30 mmHg/seconds may be computed at different pressures and volumes. During a recording time of 5 minutes these single waves may constitute 20% of single waves at one point of the horizontal part of the curve but may constitute 80% of single waves at one point of the vertical portion of the curve. Similar computations may be made for other single waves. Based on the recordings of many patients, normograms may a computed. Thereby the results from this single subject may be superimposed on the normogram of the pressure volume curve and an accurate description of elastance in this particular subject is given.

While particular embodiments of the present invention have been described herein, it is to be understood that various changes, modifications, additions and adaptations are within the scope of the present invention, as set forth in the following claims.

What is claimed is:

1. A system for performing an analysis of pressure-signals derivable from pressure measurements on or in a body of a human being or animal, said system including:
   a communication interface for receiving a set of digital pressure sample values,
   a memory for storing these values, and
      a processor capable of performing the analysis,
         said processor having means to identify features related to single pressure waves in said pressure signals based on input of said digital data into the processor,
         said processor further having determination means which based on said features is configured to:
         a) determine a minimum pressure value related to diastolic minimum value and a maximum pressure value related to systolic maximum value,
         b) determine at least one parameter of the single wave parameters elected from the group of: pressure amplitude=$\Delta P$=[(maximum pressure value)−(minimum pressure value)], latency ($\Delta T$), rise time or rise time coefficient=$\Delta P/\Delta T$, and wavelength of the single wave,
         c) determine number of said single pressure waves occurring during a given time sequence, including determination of the number of single pressure waves with pre-selected values of one or more of said single pressure wave parameters during said given time sequence, and
         d) determine number of single pressure waves with pre-selected combinations of two or more of said single pressure wave parameters during said given time sequence,
      and
   a display for visual presentation of the result of analysis performed by the processor.

2. A system according to claim 1, wherein said display is a video interface controlled by said processor.

3. A system according to claim 1, wherein said communication interface, memory, processor and display together constitute a single apparatus means.

4. A system according to claim 3, wherein a pressure sensor and pressure transducer is connectable to said apparatus.

5. A system according to claim 3, wherein said apparatus is used as an interface for connecting a network station or personal computer to a pressure sensor.

6. A system according to claim 3, wherein said apparatus is digitally operated when sampling and storing pressure measurements obtained from a pressure sensor placed in or on a patient.

7. A system according to claim 3, wherein said apparatus has an input for receiving pressure measurements from a pressure sensor capable of sensing pressures elected from intracranial pressure, blood pressure, and pressure in other body cavities of a human or animal.

8. A system according to claim 3, wherein said apparatus includes an input control.

9. A system according to claim 8, wherein said input control includes at least one of a calibration function, a function for selecting the interval of pressure recordings, and a function for adjusting the real time clock.

10. A system according to claim 3, wherein an internal battery powers said apparatus.

11. A system according to claim 10, wherein said internal battery is rechargeable.

12. A system according to claim 3, wherein said apparatus includes an input for external power supply.

13. A system according to claim 3, wherein said single apparatus means is a programmable computer.

* * * * *